United States Patent
Schooneveld-Bergmans et al.

(10) Patent No.: US 9,121,013 B2
(45) Date of Patent: Sep. 1, 2015

(54) POLYPEPTIDE HAVING BETA-GLUCOSIDASE ACTIVITY AND USES THEREOF

(75) Inventors: Margot Elisabeth Francoise Schooneveld-Bergmans, Delft (NL); Wilbert Herman Marie Heijne, Dordrecht (NL); Rene Marcel De Jong, Amsterdam (NL); Robbertus Antonius Damveld, Berkel en Rodenrijs (NL)

(73) Assignee: DSM IP ASSETS B.V., Heerlen (NL)

( * ) Notice: Subject to any disclaimer, the term of this patent is extended or adjusted under 35 U.S.C. 154(b) by 258 days.

(21) Appl. No.: 13/806,124

(22) PCT Filed: Jun. 23, 2011

(86) PCT No.: PCT/EP2011/060568
§ 371 (c)(1),
(2), (4) Date: Dec. 20, 2012

(87) PCT Pub. No.: WO2012/000886
PCT Pub. Date: Jan. 5, 2012

(65) Prior Publication Data
US 2013/0095531 A1      Apr. 18, 2013

Related U.S. Application Data

(60) Provisional application No. 61/359,567, filed on Jun. 29, 2010.

(30) Foreign Application Priority Data

Jun. 29, 2010   (EP) .................................... 10167772

(51) Int. Cl.
| | | |
|---|---|---|
| *C12N 9/38* | (2006.01) | |
| *C12N 15/00* | (2006.01) | |
| *C12N 1/14* | (2006.01) | |
| *A01H 5/00* | (2006.01) | |
| *C12N 9/42* | (2006.01) | |
| *C12S 3/00* | (2006.01) | |
| *C12P 7/10* | (2006.01) | |

(52) U.S. Cl.
CPC ................ *C12N 9/42* (2013.01); *C12N 9/2445* (2013.01); *C12Y 302/01021* (2013.01)

(58) Field of Classification Search
None
See application file for complete search history.

(56) References Cited

U.S. PATENT DOCUMENTS 8,143,050 B2 *   3/2012   Yang et al. .................... 435/209

FOREIGN PATENT DOCUMENTS

WO   2007/019442   2/2007

OTHER PUBLICATIONS

International Search Report Based on Application No. PCT/EP2011/060568 Mailed October 11, 2011.
Murray et al.; "Expression in Trichoderma reesei and Characterisation of a Thermostable Family 3 Beta-Glucosidase From the Moderately Thermophilic Fungus Talaromyces emersonii"; Protein Expression and Purification, Academic Press, San Diego, CA; Dec. 1, 2004; vol. 38; No. 2; pp. 248-257.
Harnpicharnchai et al.; "A Thermotolerant Beta-Glucosidase Isolated From an Endophytic Fungi, Periconia Sp., With a Possible Use for Biomass Conversion to Sugars"; Protein Expression and Purification, Academic Press, San Diego, CA; vol. 67; No. 2; Oct. 1, 2009; pp. 61-69.
Kawaguchi et al.; "Cloning and Sequencing of the CDNA Encoding Beta-Glucosidase 1 From Aspergillus aculeatus "; Gene; Elsevier; Amsterdam, NL; vol. 173; No. 2; Sep. 16, 1996; pp. 287-288.
Database EMBL1 [Online]; Dec. 16, 2008; "G1219P143RH11. To Neurospora crassa CDNA—7 Days Post-Cross Sexual Growth Neurospora crassa CDNA, MRNA Sequence"; Retrieved From EBI Accession No. EMBL:GE988045.

* cited by examiner

*Primary Examiner* — David H Kruse
*Assistant Examiner* — Jason Deveau Rosen
(74) *Attorney, Agent, or Firm* — Miles & Stockbridge PC

(57) ABSTRACT

The invention relates to a polypeptide comprising the amino acid sequence set out in SEQ ID NO: 2 or an amino acid sequence encoded by the nucleotide sequence of SEQ ID NO: 1, or a variant polypeptide or variant polynucleotide thereof, wherein the variant polypeptide has at least 70% sequence identity with the sequence set out in SEQ ID NO: 2 or the variant polynucleotide encodes a polypeptide that has at least 70% sequence identity with the sequence set out in SEQ ID NO: 2. The invention features the full length coding sequence of the novel gene as well as the amino acid sequence of the full-length functional polypeptide and functional equivalents of the gene or the amino acid sequence. The invention also relates to methods for using the polypeptide in industrial processes. Also included in the invention are cells transformed with a polynucleotide according to the invention suitable for producing these proteins.

28 Claims, 1 Drawing Sheet

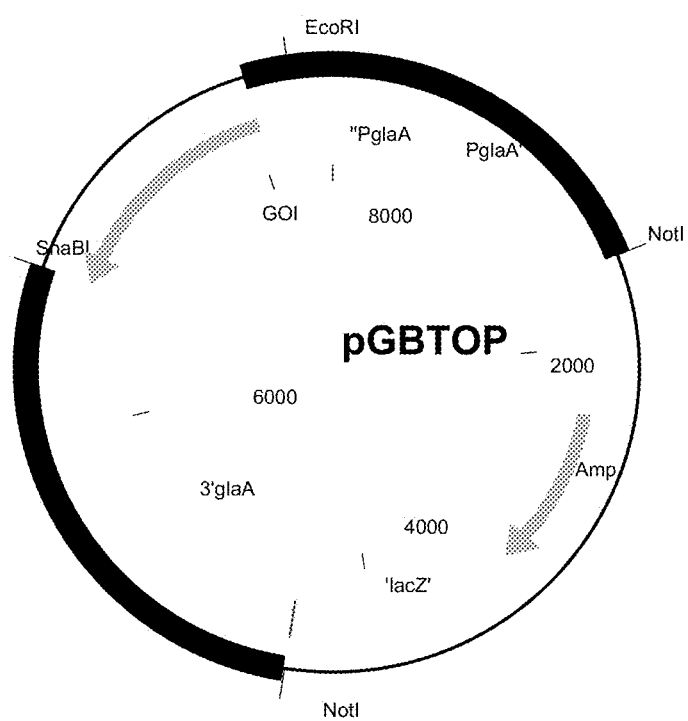

POLYPEPTIDE HAVING BETA-GLUCOSIDASE ACTIVITY AND USES THEREOF

CROSS REFERENCE TO RELATED APPLICATIONS

This application is a §371 National Stage Application of PCT/EP2011/060568 filed Jun. 23, 2011, which claims priority to U.S. Provisional Application No. 61/359,567 filed Jun. 29, 2010 and European Application No. 10167772.2, filed Jun. 29, 2010.

STATEMENT OF FEDERALLY SPONSORED RESEARCH AND DEVELOPMENT

This invention was made with US Government support under Grant no. DE-FC36-08G018079, awarded by the Department of Energy. The US Government may have certain rights in this invention.

BACKGROUND OF THE INVENTION

1. Field of the Invention

The invention relates to sequences comprising genes that encode polypeptides having or assisting in carbohydrate material degrading activity. The invention features the full-length coding sequence of the novel gene as well as the amino acid sequence of the full-length functional protein, and variants and fragments of the gene or the amino acid sequence. The invention also relates to methods for using these proteins in industrial processes. Also included in the invention are cells transformed with a polynucleotide according to the invention suitable for producing these proteins. Also the invention relates to the successful expression of the genes that encode polypeptides having carbohydrate material degrading activity in a host. The host may be any suitable host, for instance *Aspergillus* e.g. *Aspergillus niger* or *Talaromyces*, e.g. *Talaromyces emersonii*.

2. Description of Related Art

Carbohydrates constitute the most abundant organic compounds on earth. However, much of this carbohydrate is sequestered in complex polymers including starch (the principle storage carbohydrate in seeds and grain), and a collection of carbohydrates and lignin known as lignocellulose. The main carbohydrate components of lignocellulose are cellulose, hemicellulose, and pectins. These complex polymers are often referred to collectively as lignocellulose.

Bioconversion of renewable lignocellulosic biomass to a fermentable sugar that is subsequently fermented to produce alcohol (e.g., ethanol) as an alternative to liquid fuels has attracted an intensive attention of researchers since 1970s, when the oil crisis broke out because of decreasing the output of petroleum by OPEC. Ethanol has been widely used as a 10% blend to gasoline in the USA or as a neat fuel for vehicles in Brazil in the last two decades. More recently, the use of E85, an 85% ethanol blend has been implemented especially for clean city applications. The importance of fuel bioethanol will increase in parallel with increases in prices for oil and the gradual depletion of its sources. Additionally, fermentable sugars are being used to produce plastics, polymers and other biobased products and this industry is expected to grow substantially therefore increasing the demand for abundant low cost fermentable sugars which can be used as a feed stock in lieu of petroleum based feedstocks.

The sequestration of such large amounts of carbohydrates in plant biomass provides a plentiful source of potential energy in the form of sugars, both five carbon and six carbon sugars that could be utilized for numerous industrial and agricultural processes. However, the enormous energy potential of these carbohydrates is currently under-utilized because the sugars are locked in complex polymers, and hence are not readily accessible for fermentation. Methods that generate sugars from plant biomass would provide plentiful, economically-competitive feedstocks for fermentation into chemicals, plastics, such as for instance succinic acid and (bio) fuels, including ethanol, methanol, butanol synthetic liquid fuels and biogas.

Regardless of the type of cellulosic feedstock, the cost and hydrolytic efficiency of enzymes are major factors that restrict the commercialization of the biomass bioconversion processes. The production costs of microbially produced enzymes are tightly connected with a productivity of the enzyme-producing strain and the final activity yield in the fermentation broth.

In spite of the continued research of the last few decades to understand enzymatic lignocellulosic biomass degradation and cellulase production, it remains desirable to discover or to engineer new highly active cellulases and hemicellulases. It would also be highly desirable to construct highly efficient enzyme compositions capable of performing rapid and efficient biodegradation of lignocellulosic materials, in particular such cellulases and hemicellulases that have increased thermostability.

Such enzymes may be used to produce sugars for fermentation into chemicals, plastics, such as for instance succinic acid and (bio) fuels, including ethanol, methanol, butanol, synthetic liquid fuels and biogas, for ensiling, and also as enzyme in other industrial processes, for example in the food or feed, textile, pulp or paper or detergent industries and other industries.

SUMMARY OF THE INVENTION

The present invention provides polynucleotides encoding polypeptides having the ability to degrade (i.e. assist in the degradation of), a carbohydrate (for example polysaccharides), in particular, lignocellulose. Polynucleotides of the invention typically encode a polypeptide having beta-glucosidase activity.

The invention also provides naturally and recombinantly produced polypeptides having such activity, as well as recombinant cell lines producing such enzymes. Also, methods of making and using the polynucleotides and polypeptides of the invention are provided.

According to the invention, there is thus provided a polypeptide which comprises the amino acid sequence set out in SEQ ID NO: 2 or an amino acid sequence encoded by the nucleotide sequence of SEQ ID NO: 1, or a variant polypeptide or variant polynucleotide thereof, wherein the variant polypeptide has at least 70% sequence identity with the sequence set out in SEQ ID NO: 2 or the variant polynucleotide encodes a polypeptide that has at least 70% sequence identity with the sequence set out in SEQ ID NO: 2.

The polypeptides according to the invention have favourable properties, in particular a cellulose degrading activity. In an embodiment, the polypeptide according to the invention has beta-glucosidase (abbreviated BG) activity.

Herein, beta-glucosidase also β-glucosidase (EC 3.2.1.21) is any polypeptide which is capable of catalysing the hydrolysis of terminal, non-reducing β-D-glucose residues with release of β-D-glucose. Such a polypeptide may have a wide specificity for β-D-glucosides and may also hydrolyze one or more of the following: a β-D-galactoside, an α-L-arabinoside, a β-D-xyloside or a β-D-fucoside. This enzyme may also be referred to as amygdalase, β-D-glucoside glucohydrolase, cellobiase or gentiobiase.

In an embodiment the variant polypeptide has a catalytic residue Asp276-Glu508 (positions as in SEQ ID NO: 2).

In an embodiment the variant polypeptide has at least 70% sequence identity with the sequence set out in SEQ ID NO: 2, a catalytic residue Asp276-Glu508 and BG activity.

Further the polypeptides may have a high thermostability. The polypeptides according the invention may retain a high relative activity (% of initial activity) of as function of incubation time (h), e.g. 2 hours, 3 hours, 4 hours, five hours, six hours, eight hours, nine hours, 10 h or more, 20 h or more, 30 h or more in particular at high temperatures, for instance at 60° C. or more at 65° C. or more, or at 70° C. or more e.g. 8 hours at 65° C. or 72 hours at 60° C.

The invention also provides a polynucleotide which comprises:
(a) the nucleotide sequence set out in SEQ ID NO: 1; or
(b) a nucleotide sequence which hybridizes selectively with a polynucleotide being the reverse complement of SEQ ID NO: 1; or
(c) a nucleotide sequence having at least about 75% sequence identity with the nucleotide sequence of SEQ ID NO: 1; or
(d) a fragment of a nucleotide sequence as defined in (a), (b) or (c) which is at least about 100 nucleotides in length; or
(e) a sequence which is degenerate as a result of the genetic code to a sequence as defined in any one of (a), (b), (c) or (d); or
(f) a nucleotide sequence which is the reverse complement of a nucleotide sequence as defined in (a), (b), (c), (d) or (e).

Also provided according to the invention is a vector, such as an expression vector, incorporating a polynucleotide sequence of the invention and a cell comprising a polypeptide, a polynucleotide or a vector of the invention.

The invention also provides:
a method for the preparation of a polypeptide having beta-glucosidase activity, which method comprises cultivating a cell of the invention under conditions which allow for expression of said polypeptide and, optionally, recovering the expressed polypeptide;
a polypeptide obtainable by such a method; and
a composition comprising: (i) a polypeptide of the invention and; (ii) a cellulase and/or a hemicellulase and/or a pectinase;

The polypeptides of the invention having beta-glucosidase activity may be used in industrial processes. Thus, the invention provides a method for the treatment of a substrate comprising carbohydrate material which method comprises contacting the substrate with a polypeptide or a composition of the invention.

In particular, the invention provides a method for producing a sugar or sugars from lignocellulosic material which method comprises contacting the lignocellulosic material with a polypeptide or a composition of the invention.

Sugars produced in this way may be used in a fermentation process. Accordingly, the invention provides a method for producing a fermentation product, which method comprises: producing a fermentable sugar using the described above; and fermenting the resulting fermentable sugar, thereby to produce a fermentation product.

A polypeptide or a composition of the invention may also be used, for example, in the preparation of a food product, in the preparation of a detergent, in the preparation of an animal feed, in the treatment of pulp or in the manufacture of a paper or in the preparation of a fabric or textile or in the cleaning thereof.

The invention also provides:
a processed material obtainable by contacting a plant material or lignocellulosic material with a polypeptide or a composition of the invention;
a food or feed comprising a polypeptide or a composition of the invention; and
a plant or a part thereof which comprises a polynucleotide, a polypeptide, a vector or a cell according to the invention.

BRIEF DESCRIPTION OF THE DRAWINGS

FIG. 1: Map of pGBTOP for expression of genes in *A. niger*. Depicted are the gene of interest (GOI) expressed from the glucoamylase promoter (PglaA). In addition, the glucoamylase flank (3'glaA) of the expression cassette is depicted. In this application a gene of interest is the coding sequence of TEMER06387 as defined hereinafter.

BRIEF DESCRIPTION OF THE SEQUENCE LISTING

SEQ ID NO: 1 sets out the coding sequence of TEMER06387;
SEQ ID NO: 2 sets out the amino acid sequence of TEMER06387;
SEQ ID NO: 3 sets out the signal sequence of TEMER06387;
SEQ ID NO:4 sets out the sequence of a translational initiator sequence;
SEQ ID NO:5 sets out the sequence of a translational initiator sequence;
SEQ ID NO:6 sets out the sequence of a translational initiator sequence.

DETAILED DESCRIPTION OF A PREFERRED EMBODIMENT

Throughout the present specification and the accompanying claims, the words "comprise" and "include" and variations such as "comprises", "comprising", "includes" and "including" are to be interpreted inclusively. That is, these words are intended to convey the possible inclusion of other elements or integers not specifically recited, where the context allows.

The articles "a" and "an" are used herein to refer to one or to more than one (i.e. to one or at least one) of the grammatical object of the article. By way of example, "an element" may mean one element or more than one element.

The present invention provides polynucleotides encoding polypeptides, e.g. enzymes which have the ability to modify, for example degrade, a carbohydrate material. A carbohydrate material is a material which comprises, consists of or substantially consists of one or more carbohydrates. Enzymes are herein a subclass of polypeptides.

Substrate (also called feedstock) herein is used to refer to a substance that comprises carbohydrate material, which may be treated with enzymes according to the invention, so that the carbohydrate material therein is modified. In addition to the carbohydrate material the substrate may contain any other component, including but not limited to non-carbohydrate material and starch.

The present invention provides polynucleotides encoding polypeptides, e.g. enzymes which have the ability to modify, for example degrade, a carbohydrate material. A carbohydrate material is a material which comprises, consists of or substantially consists of one or more carbohydrates. Enzymes are herein a subclass of polypeptides.

Typically, a polypeptide of the invention encodes a polypeptide having at least beta-glucosidase activity, tentatively called TEMER06387, having an amino acid sequence according to SEQ ID NO: 2, or a sequence which is a variant thereof, typically functionally equivalent to the polypeptide having the sequence of SEQ ID NO: 2, or a sequence which is a fragment of either thereof.

In an embodiment, a polypeptide of the invention may have one or more alternative and/or additional activities other than that of beta-glucosidase activity as mentioned before, for example one of the other carbohydrate degrading and/or carbohydrate hydrolysing activities mentioned herein.

Carbohydrate in this context includes all saccharides, for example polysaccharides, oligosaccharides, disaccharides or monosaccharides.

A polypeptide according to the invention may modify and/or degrade a carbohydrate material by chemically degrading or physically degrading such material or hydrolysing the carbohydrate. Physical includes e.g. interruption of interaction between cellulose microfibrils and/or opening up the cellulose fiber structure. Chemical modification of the carbohydrate material may result in the degradation of such material, for example by hydrolysis, oxidation or other chemical modification such as by the action of a lyase. Physical modification may or may not be accompanied by chemical modification.

Suitable Carbohydrate Materials

A non-starch carbohydrate suitable for modification by a polypeptide of the invention is lignocellulose. The major polysaccharides comprising different lignocellulosic residues, which may be considered as a potential renewable feedstock, are cellulose (glucans), hemicelluloses (xylans, heteroxylans and xyloglucans). In addition, some hemicellulose may be present as glucomannans, for example in wood-derived feedstocks. The enzymatic hydrolysis of these polysaccharides to soluble sugars, for example glucose, xylose, arabinose, galactose, fructose, mannose, rhamnose, ribose, D-galacturonic acid and other hexoses and pentoses occurs under the action of different enzymes acting in concert.

In addition, pectins and other pectic substances such as arabinans may make up considerably proportion of the dry mass of typically cell walls from non-woody plant tissues (about a quarter to half of dry mass may be pectins).

Cellulose is a linear polysaccharide composed of glucose residues linked by β-1,4 bonds. The linear nature of the cellulose fibers, as well as the stoichiometry of the β-linked glucose (relative to α) generates structures more prone to interstrand hydrogen bonding than the highly branched α-linked structures of starch. Thus, cellulose polymers are generally less soluble, and form more tightly bound fibers than the fibers found in starch.

Hemicellulose is a complex polymer, and its composition often varies widely from organism to organism, and from one tissue type to another. In general, a main component of hemicellulose is β-1,4-linked xylose, a five carbon sugar. However, this xylose is often branched at O-3 and/or O-2 and can be substituted with linkages to arabinose, galactose, mannose, glucuronic acid, galacturonic acid or by esterification to acetic acid (and esterification of ferulic acid to arabinose). Hemicellulose can also contain glucan, which is a general term for β-linked six carbon sugars (such as the β-(1,3)(1,4) glucans and heteroglucans mentioned previously) and additionally glucomannans (in which both glucose and mannose are present in the linear backbone, linked to each other by β-linkages).

The composition, nature of substitution, and degree of branching of hemicellulose is very different in dicotyledonous plants (dicots, i.e., plant whose seeds have two cotyledons or seed leaves such as lima beans, peanuts, almonds, peas, kidney beans) as compared to monocotyledonous plants (monocots; i.e., plants having a single cotyledon or seed leaf such as corn, wheat, rice, grasses, barley). In dicots, hemicellulose is comprised mainly of xyloglucans that are 1,4-β-linked glucose chains with 1,6-β-linked xylosyl side chains. In monocots, including most grain crops, the principal components of hemicellulose are heteroxylans. These are primarily comprised of 1,4-β-linked xylose backbone polymers with 1,3-α linkages to arabinose, galactose, mannose and glucuronic acid or 4-O-methyl-glucuronic acid as well as xylose modified by ester-linked acetic acids. Also present are β glucans comprised of 1,3- and 1,4-β-linked glucosyl chains. In monocots, cellulose, heteroxylans and β-glucans may be present in roughly equal amounts, each comprising about 15-25% of the dry matter of cell walls. Also, different plants may comprise different amounts of, and different compositions of, pectic substances. For example, sugar beet contains about 19% pectin and about 21% arabinan on a dry weight basis.

Accordingly, a composition of the invention may be tailored in view of the particular feedstock (also called substrate) which is to be used. That is to say, the spectrum of activities in a composition of the invention may vary depending on the feedstock in question.

Enzyme combinations or physical treatments can be administered concomitantly or sequentially. The enzymes can be produced either exogenously in microorganisms, yeasts, fungi, bacteria or plants, then isolated and added to the lignocellulosic feedstock. Alternatively, the enzymes are produced, but not isolated, and crude cell mass fermentation broth, or plant material (such as corn stover), and the like are added to the feedstock. Alternatively, the crude cell mass or enzyme production medium or plant material may be treated to prevent further microbial growth (for example, by heating or addition of antimicrobial agents), then added to the feedstock. These crude enzyme mixtures may include the organism producing the enzyme. Alternatively, the enzyme may be produced in a fermentation that uses feedstock (such as corn stover) to provide nutrition to an organism that produces an enzyme(s). In this manner, plants that produce the enzymes may serve as the lignocellulosic feedstock and be added into lignocellulosic feedstock.

Enzymatic Activity

Endo-1,4-β-glucanases (EG) and exo-cellobiohydrolases (CBH) catalyze the hydrolysis of insoluble cellulose to cellooligosaccharides (cellobiose as a main product), while β-glucosidases (BGL) convert the oligosaccharides, mainly cellobiose and cellotriose to glucose.

Xylanases together with other accessory enzymes, for example α-L-arabinofuranosidases, feruloyl and acetylxylan esterases, glucuronidases, and β-xylosidases) catalyze the hydrolysis of part of the hemicelluloses.

Pectic substances include pectins, arabinans, galactans and arabinogalactans. Pectins are the most complex polysaccharides in the plant cell wall. They are built up around a core chain of α(1,4)-linked D-galacturonic acid units interspersed to some degree with L-rhamnose. In any one cell wall there are a number of structural units that fit this description and it has generally been considered that in a single pectic molecule, the core chains of different structural units are continuous with one another.

Pectinases include, for example an endo polygalacturonase, a pectin methyl esterase, an endo-galactanase, a beta galactosidase, a pectin acetyl esterase, an endo-pectin lyase, pectate lyase, alpha rhamnosidase, an exo-galacturonase, an expolygalacturonate lyase, a rhamnogalacturonan hydrolase, a rhamnogalacturonan lyase, a rhamnogalacturonan acetyl esterase, a rhamnogalacturonan galacturonohydrolase, a xylogalacturonase, an α-arabinofuranosidase.

The principal types of structural unit are: galacturonan (homogalacturonan), which may be substituted with methanol on the carboxyl group and acetate on O-2 and O-3; rhamnogalacturonan I (RGI), in which galacturonic acid units alternate with rhamnose units carrying (1,4)-linked galactan and (1,5)-linked arabinan side-chains. The arabinan side-chains may be attached directly to rhamnose or indirectly through the galactan chains; xylogalacturonan, with single xylosyl units on O-3 of galacturonic acid (closely associated with RGI); and rhamnogalacturonan II (RGII), a particularly complex minor unit containing unusual sugars, for example apiose. An RGII unit may contain two apiosyl residues which, under suitable ionic conditions, can reversibly form esters with borate.

As set out above, a polypeptide of the invention will typically have beta-glucosidase activity. However, a polypeptide of the invention may have one or more of the activities set out above in addition to or alternative to that activity. Also, a composition of the invention as described herein may have one or more of the activities mentioned above in addition to that provided by a polypeptide of the invention having beta-glucosidase activity.

Polynucleotide Sequence

The invention provides genomic polynucleotide sequences comprising the gene encoding the TEMER06387 as well as its coding sequence. Accordingly, the invention relates to an isolated polynucleotide comprising the genomic nucleotide sequence according to the coding nucleotide sequence according to SEQ ID NO: 1 and to variants, such as functional equivalents, of either thereof.

In particular, the invention relates to an isolated polynucleotide which is capable of hybridizing selectively, for example under stringent conditions, preferably under highly stringent conditions, with the reverse complement of a polynucleotide comprising the sequence set out in SEQ ID NO: 1.

More specifically, the invention relates to a polynucleotide comprising or consisting essentially of a nucleotide sequence according to SEQ ID NO: 1.

The invention also relates to an isolated polynucleotide comprising or consisting essentially of a sequence which encodes at least one functional domain of a polypeptide according to SEQ ID NO: 2 or a variant thereof, such as a functional equivalent, or a fragment of either thereof.

As used herein, the terms "gene" and "recombinant gene" refer to nucleic acid molecules which may be isolated from chromosomal DNA, which include an open reading frame encoding a protein, e.g. the beta-glucosidase protein according to the present invention.

A gene may include coding sequences, non-coding sequences, introns and/or regulatory sequences. Moreover, the term "gene" may refer to an isolated nucleic acid molecule as defined herein.

A nucleic acid molecule of the present invention, such as a nucleic acid molecule having the nucleotide sequence of SEQ ID NO: 1 or a variant thereof, such as a functional equivalent, can be isolated using standard molecular biology techniques and the sequence information provided herein. For example, using all or a portion of the nucleic acid sequence of SEQ ID NO: 1 as a hybridization probe, nucleic acid molecules according to the invention can be isolated using standard hybridization and cloning techniques (e.g., as described in Sambrook, J., Fritsh, E. F., and Maniatis, T. Molecular Cloning: A Laboratory Manual. 2nd, ed., Cold Spring Harbor Laboratory, Cold Spring Harbor Laboratory Press, Cold Spring Harbor, N.Y., 1989).

Moreover, a nucleic acid molecule encompassing all or a portion of SEQ ID NO: 1 may be isolated by the polymerase chain reaction (PCR) using synthetic oligonucleotide primers designed based upon the sequence information contained in SEQ ID NO: 1.

A nucleic acid of the invention can be amplified using cDNA, mRNA or alternatively, genomic DNA, as a template and appropriate oligonucleotide primers according to standard PCR amplification techniques. The nucleic acid so amplified can be cloned into an appropriate vector and characterized by DNA sequence analysis.

Furthermore, oligonucleotides corresponding to or hybridizable to a nucleotide sequence according to the invention can be prepared by standard synthetic techniques, e.g., using an automated DNA synthesizer.

In a preferred embodiment, an isolated nucleic acid molecule of the invention comprises the nucleotide sequence shown in SEQ ID NO: 1.

In another preferred embodiment, an isolated nucleic acid molecule of the invention comprises a nucleic acid molecule which is the reverse complement of the nucleotide sequence shown in SEQ ID NO: 1 or a variant, such as a functional equivalent, of either such nucleotide sequence.

A nucleic acid molecule which is complementary to another nucleotide sequence is one which is sufficiently complementary to the other nucleotide sequence such that it can hybridize to the other nucleotide sequence thereby forming a stable duplex.

One aspect of the invention pertains to isolated nucleic acid molecules that encode a polypeptide of the invention or a variant, such as a functional equivalent thereof, for example a biologically active fragment or domain, as well as nucleic acid molecules sufficient for use as hybridization probes to identify nucleic acid molecules encoding a polypeptide of the invention and fragments of such nucleic acid molecules suitable for use as PCR primers for the amplification or mutation of nucleic acid molecules.

A polynucleotide according to the invention may be "isolated". In the context of this invention, an "isolated polynucleotide" or "isolated nucleic acid" is a DNA or RNA that is not immediately contiguous with one or both of the coding sequences with which it is immediately contiguous (one on the 5' end and one on the 3' end) in the naturally occurring genome of the organism from which it is derived. Thus, in one embodiment, an isolated nucleic acid includes some or all of the 5' non-coding (e.g. promotor) sequences that are immediately contiguous to the coding sequence. The term therefore includes, for example, a recombinant DNA that is incorporated into a vector, into an autonomously replicating plasmid or virus, or into the genomic DNA of a prokaryote or eukaryote, or which exists as a separate molecule (e.g., a cDNA or a genomic DNA fragment produced by PCR or restriction endonuclease treatment) independent of other sequences. It also includes a recombinant DNA that is part of a hybrid gene encoding an additional polypeptide that is substantially free of cellular material, viral material, or culture medium (when produced by recombinant DNA techniques), or chemical precursors or other chemicals (when chemically synthesized). Moreover, an "isolated nucleic acid fragment" is a nucleic acid fragment that is not naturally occurring as a fragment and would not be found in the natural state.

As used herein, the terms "polynucleotide" or "nucleic acid molecule" are intended to include DNA molecules (e.g., cDNA or genomic DNA) and RNA molecules (e.g., mRNA) and analogs of the DNA or RNA generated using nucleotide analogs. The nucleic acid molecule can be single-stranded or double-stranded, but preferably is double-stranded DNA. The nucleic acid may be synthesized using oligonucleotide analogs or derivatives (e.g., inosine or phosphorothioate nucleotides). Such oligonucleotides can be used, for example, to prepare nucleic acids that have altered base-pairing abilities or increased resistance to nucleases.

Another embodiment of the invention provides an isolated nucleic acid molecule which is antisense to a TEMER06387 nucleic acid molecule, e.g., the coding strand of a TEMER06387 nucleic acid molecule. Also included within the scope of the invention are the complementary strands of the nucleic acid molecules described herein.

Unless otherwise indicated, all nucleotide sequences determined by sequencing a DNA molecule herein were determined using an automated DNA sequencer and all amino acid sequences of polypeptides encoded by DNA molecules determined herein were predicted by translation of a DNA sequence determined as above. Therefore, as is known in the art for any DNA sequence determined by this automated approach, any nucleotide sequence determined herein may contain some errors. Nucleotide sequences determined by automation are typically at least about 90% identical, more typically at least about 95% to at least about 99.9% identical to the actual nucleotide sequence of the sequenced DNA molecule.

The actual sequence can be more precisely determined by other approaches including manual DNA sequencing methods well known in the art. As is also known in the art, a single insertion or deletion in a determined nucleotide sequence compared to the actual sequence will cause a frame shift in translation of the nucleotide sequence such that the predicted amino acid sequence encoded by a determined nucleotide sequence will be completely different from the amino acid sequence actually encoded by the sequenced DNA molecule, beginning at the point of such an insertion or deletion.

The person skilled in the art is capable of identifying such erroneously identified bases and knows how to correct for such errors.

A nucleic acid molecule according to the invention may comprise only a portion or a fragment of the nucleic acid sequence shown in SEQ ID NO: 1 (or of a variant of either thereof), for example a fragment which can be used as a probe or primer or a fragment encoding a portion of a TEMER06387 polypeptide.

The nucleotide sequence determined from the cloning of the TEMER06387 gene and cDNA allows for the generation of probes and primers designed for use in identifying and/or cloning other TEMER06387 family members, as well as TEMER06387 homologues from other species.

The probe/primer typically comprises a substantially purified oligonucleotide which typically comprises a region of nucleotide sequence that hybridizes preferably under highly stringent conditions to at least from about 12 to about 15, preferably from about 18 to about 20, preferably from about 22 to about 25, more preferably about 30, about 35, about 40, about 45, about 50, about 55, about 60, about 65, or about 75 or more consecutive nucleotides of a nucleotide sequence shown in SEQ ID NO: 1 or of a variant, such as a functional equivalent, of either thereof.

Probes based on the TEMER06387 nucleotide sequences can be used to detect transcripts or genomic TEMER06387 sequences encoding the same or homologous polypeptides for instance in other organisms. In preferred embodiments, the probe further comprises a label group attached thereto, e.g., the label group can be a radioisotope, a fluorescent compound, an enzyme, or an enzyme cofactor. Such probes can also be used as part of a diagnostic test kit for identifying cells which express a TEMER06387 polypeptide.

The polynucleotides herein may be synthetic polynucleotides. The synthetic polynucleotides may be optimized in codon use, preferably according to the methods described in WO2006/077258 and/or PCT/EP2007/055943, which are herein incorporated by reference. PCT/EP2007/055943 addresses codon-pair optimization. Codon-pair optimization is a method wherein the nucleotide sequences encoding a polypeptide have been modified with respect to their codon-usage, in particular the codon-pairs that are used, to obtain improved expression of the nucleotide sequence encoding the polypeptide and/or improved production of the encoded polypeptide. Codon pairs are defined as a set of two subsequent triplets (codons) in a coding sequence.

The invention further relates to a nucleic acid construct comprising the polynucleotide as described before. "Nucleic acid construct" is defined herein as a nucleic acid molecule, either single- or double-stranded, which is isolated from a naturally occurring gene or which has been modified to contain segments of nucleic acid which are combined and juxtaposed in a manner which would not otherwise exist in nature. The term nucleic acid construct is synonymous with the term "expression cassette" when the nucleic acid construct contains all the control sequences required for expression of a coding sequence. The term "coding sequence" as defined herein is a sequence, which is transcribed into mRNA and translated into a transcriptional activator of a protease promoter of the invention. The boundaries of the coding sequence are generally determined by the ATG start codon at the 5'end of the mRNA and a translation stop codon sequence terminating the open reading frame at the 3'end of the mRNA. A coding sequence can include, but is not limited to, DNA, cDNA, and recombinant nucleic acid sequences. Preferably, the nucleic acid has high GC content. The GC content herein indicates the number of G and C nucleotides in the construct, divided by the total number of nucleotides, expressed in %. The GC content is preferably 56% or more, 57% or more, 58% or more, 59% or more, 60% or more, or in the range of 56-70% or the range of 58-65%.

Preferably, the DNA construct comprises a promoter DNA sequence, a coding sequence in operative association with said promoter DNA sequence and control sequences such as:
  one translational termination sequence orientated in 5' towards 3' direction selected from the following list of sequences: TAAG, TAGA and TAAA, preferably TAAA, and/or
  one translational initiator coding sequence orientated in 5' towards 3' direction selected from the following list of sequences: GCTACCCCC; GCTACCTCC; GCTAC-CCTC; GCTACCTTC; GCTCCCCCC; GCTCCCTCC; GCTCCCCTC; GCTCCCTTC; GCTGCCCCC; GCT-GCCTCC; GCTGCCCTC; GCTGCCTTC; GCTTC-CCCC; GCTTCCTCC; GCTTCCCTC; and GCTTC-CTTC, preferably GCT TCC TTC, and/or
  one translational initiator sequence selected from the following list of sequences: 5'-mwChkyCAAA-3' (SEQ ID NO:4); 5'-mwChkyCACA-3' (SEQ ID NO:5) or 5'-mwChkyCAAG-3' (SEQ ID NO:6), using ambiguity codes for nucleotides: m (A/C); w (A/T); y (C/T); k (G/T); h (A/C/T), preferably 5'-CACCGTCAAA-3' (see, e.g., SEQ ID NO:4) or 5'-CGCAGTCAAG-3' (see, e.g., SEQ ID NO:6).

In the context of this invention, the term "translational initiator coding sequence" is defined as the nine nucleotides immediately downstream of the initiator or start codon of the open reading frame of a DNA coding sequence. The initiator or start codon encodes for the AA methionine. The initiator codon is typically ATG, but may also be any functional start codon such as GTG.

In the context of this invention, the term "translational termination sequence" is defined as the four nucleotides starting from the translational stop codon at the 3' end of the open reading frame or nucleotide coding sequence and oriented in 5' towards 3' direction.

In the context of this invention, the term "translational initiator sequence" is defined as the ten nucleotides immediately upstream of the initiator or start codon of the open reading frame of a DNA sequence coding for a polypeptide. The initiator or start codon encodes for the AA methionine. The initiator codon is typically ATG, but may also be any functional start codon such as GTG. It is well known in the art that uracil, U, replaces the deoxynucleotide thymine, T, in RNA.

Homology and Identity

Amino acid or nucleotide sequences are said to be homologous when exhibiting a certain level of similarity. Two sequences being homologous indicate a common evolutionary origin. Whether two homologous sequences are closely related or more distantly related is indicated by "percent identity" or "percent similarity", which is high or low respectively. Although disputed, to indicate "percent identity" or "percent similarity", "level of homology" or "percent homology" are frequently used interchangeably.

The terms "homology", "percent homology", "percent identity" or "percent similarity" are used interchangeably herein. For the purpose of this invention, it is defined here that in order to determine the percent identity of two amino acid sequences or of two nucleic acid sequences, the complete sequences are aligned for optimal comparison purposes. In order to optimize the alignment between the two sequences gaps may be introduced in any of the two sequences that are compared. Such alignment is carried out over the full length of the sequences being compared. Alternatively, the alignment may be carried out over a shorter length, for example over about 20, about 50, about 100 or more nucleic acids/based or amino acids. The identity is the percentage of identical matches between the two sequences over the reported aligned region.

A comparison of sequences and determination of percent identity between two sequences can be accomplished using a mathematical algorithm. The skilled person will be aware of the fact that several different computer programs are available to align two sequences and determine the homology between two sequences (Kruskal, J. B. (1983) An overview of sequence comparison In D. Sankoff and J. B. Kruskal, (ed.), Time warps, string edits and macromolecules: the theory and practice of sequence comparison, pp. 1-44 Addison Wesley). The percent identity between two amino acid sequences can be determined using the Needleman and Wunsch algorithm for the alignment of two sequences. (Needleman, S. B. and Wunsch, C. D. (1970) J. Mol. Biol. 48, 443-453). The algorithm aligns amino acid sequences as well as nucleotide sequences. The Needleman-Wunsch algorithm has been implemented in the computer program NEEDLE. For the purpose of this invention the NEEDLE program from the EMBOSS package was used (version 2.8.0 or higher, EMBOSS: The European Molecular Biology Open Software Suite (2000) Rice, P. Longden, I. and Bleasby, A. Trends in Genetics 16, (6) pp 276-277, emboss.bioinfomatics.nl/). For polypeptide sequences, BLOSUM62 is used for the substitution matrix. For nucleotide sequences, EDNAFULL is used. Other matrices can be specified. The optional parameters used for alignment of amino acid sequences are a gap-open penalty of 10 and a gap extension penalty of 0.5. The skilled person will appreciate that all these different parameters will yield slightly different results but that the overall percentage identity of two sequences is not significantly altered when using different algorithms.

Global Homology Definition

The homology or identity is the percentage of identical matches between the two full sequences over the total aligned region including any gaps or extensions. The homology or identity between the two aligned sequences is calculated as follows: Number of corresponding positions in the alignment showing an identical amino acid in both sequences divided by the total length of the alignment including the gaps. The identity defined as herein can be obtained from NEEDLE and is labelled in the output of the program as "IDENTITY".

Longest Identity Definition

The homology or identity between the two aligned sequences is calculated as follows: Number of corresponding positions in the alignment showing an identical amino acid in both sequences divided by the total length of the alignment after subtraction of the total number of gaps in the alignment. The identity defined as herein can be obtained from NEEDLE by using the NOBRIEF option and is labelled in the output of the program as "longest-identity". For purposes of the invention the level of identity (homology) between two sequences (amino acid or nucleotide) is calculated according to the definition of "longest-identity" as can be carried out by using the program NEEDLE.

The polypeptide sequences of the present invention can further be used as a "query sequence" to perform a search against sequence databases, for example to identify other family members or related sequences. Such searches can be performed using the BLAST programs. Software for performing BLAST analyses is publicly available through the National Center for Biotechnology Information (ncbi.nlm.nih.gov). BLASTP is used for amino acid sequences and BLASTN for nucleotide sequences. The BLAST program uses as defaults:

Cost to open gap: default=5 for nucleotides/11 for polypeptides
Cost to extend gap: default=2 for nucleotides/1 for polypeptides
Penalty for nucleotide mismatch: default=−3
Reward for nucleotide match: default=1
Expect value: default=10
Wordsize: default=11 for nucleotides/28 for megablast/3 for polypeptides Furthermore the degree of local identity (homology) between the amino acid sequence query or nucleic acid sequence query and the retrieved homologous sequences is determined by the BLAST program. However only those sequence segments are compared that give a match above a certain threshold. Accordingly the program calculates the identity only for these matching segments. Therefore the identity calculated in this way is referred to as local identity.

Hybridization

As used herein, the term "selectively hybridizing", "hybridizes selectively" and similar terms are intended to describe conditions for hybridization and washing under which nucleotide sequences at least about 50%, at least about 55%, at least about 60%, at least about 65%, at least about 70%, at least about 75%, at least about 80%, more preferably at least about 85%, even more preferably at least about 90%, preferably at least 95%, more preferably at least about 98% or more preferably at least about 99% homologous to each other typically remain hybridized to each other. That is to say, such hybridizing sequences may share at least about 50%, at least about 55%, at least about 60%, at least about 65%, at least about 70%, at least about 75%, at least about 80%, more preferably at least about 85%, even more preferably at least about 90%, more preferably at least 95%, more preferably at least 98% or more preferably at least about 99% sequence identity.

A preferred, non-limiting example of such hybridization conditions is hybridization in 6× sodium chloride/sodium citrate (SSC) at about 45° C., followed by one or more washes in 1×SSC, 0.1% SDS at about 50° C., preferably at about 55° C., preferably at about 60° C. and even more preferably at about 65° C.

Highly stringent conditions include, for example, hybridization at about 68° C. in 5×SSC/5×Denhardt's solution/1.0% SDS and washing in 0.2×SSC/0.1% SDS at room temperature. Alternatively, washing may be performed at 42° C.

The skilled artisan will know which conditions to apply for stringent and highly stringent hybridization conditions. Additional guidance regarding such conditions is readily available in the art, for example, in Sambrook et al., 1989, Molecular Cloning, A Laboratory Manual, Cold Spring Harbor Press, N.Y.; and Ausubel et al. (eds.), 1995, Current Protocols in Molecular Biology, (John Wiley & Sons, N.Y.).

Of course, a polynucleotide which hybridizes only to a poly A sequence (such as the 3' terminal poly(A) tract of mRNAs), or to a complementary stretch of T (or U) resides, would not be included in a polynucleotide of the invention used to specifically hybridize to a portion of a nucleic acid of the invention, since such a polynucleotide would hybridize to any nucleic acid molecule containing a poly (A) stretch or the complement thereof (e.g., practically any double-stranded cDNA clone).

In a typical approach, cDNA libraries constructed from other organisms, e.g. a filamentous fungi, in particular from the micro-organism family Trichomaceae, for example from the genus *Penicillium* can be screened such as *Penicillium decumbens*.

For example, *Penicillium* strains can be screened for homologous TEMER06387 polynucleotides by Northern blot analysis. Upon detection of transcripts homologous to polynucleotides according to the invention, cDNA libraries can be constructed from RNA isolated from the appropriate strain, utilizing standard techniques well known to those of skill in the art. Alternatively, a total genomic DNA library can be screened using a probe capable of hybridizing to a TEMER06387 polynucleotide according to the invention.

Homologous gene sequences can be isolated, for example, by performing PCR using two degenerate oligonucleotide primer pools designed on the basis of nucleotide sequences as taught herein.

The template for the reaction can be cDNA obtained by reverse transcription of mRNA prepared from strains known or suspected to express a polynucleotide according to the invention. The PCR product can be subcloned and sequenced to ensure that the amplified sequences represent the sequences of a new TEMER06387 nucleic acid sequence, or a functional equivalent thereof.

The PCR fragment can then be used to isolate a full-length cDNA clone by a variety of known methods. For example, the amplified fragment can be labeled and used to screen a bacteriophage or cosmid cDNA library. Alternatively, the labeled fragment can be used to screen a genomic library.

PCR technology also can be used to isolate full-length cDNA sequences from other organisms. For example, RNA can be isolated, following standard procedures, from an appropriate cellular or tissue source. A reverse transcription reaction can be performed on the RNA using an oligonucleotide primer specific for the most 5' end of the amplified fragment for the priming of first strand synthesis.

The resulting RNA/DNA hybrid can then be "tailed" (e.g., with guanines) using a standard terminal transferase reaction, the hybrid can be digested with RNase H, and second strand synthesis can then be primed (e.g., with a poly-C primer). Thus, cDNA sequences upstream of the amplified fragment can easily be isolated. For a review of useful cloning strategies, see e.g., Sambrook et al., supra; and Ausubel et al., supra.

Vectors

Another aspect of the invention pertains to vectors, including cloning and expression vectors, comprising a polynucleotide of the invention encoding a TEMER06387 polypeptide or a functional equivalent thereof and methods of growing, transforming or transfecting such vectors in a suitable host cell, for example under conditions in which expression of a polypeptide of the invention occurs. As used herein, the term "vector" refers to a nucleic acid molecule capable of transporting another nucleic acid to which it has been linked.

Polynucleotides of the invention can be incorporated into a recombinant replicable vector, for example a cloning or expression vector. The vector may be used to replicate the nucleic acid in a compatible host cell. Thus in a further embodiment, the invention provides a method of making polynucleotides of the invention by introducing a polynucleotide of the invention into a replicable vector, introducing the vector into a compatible host cell, and growing the host cell under conditions which bring about replication of the vector. The vector may be recovered from the host cell. Suitable host cells are described below.

The vector into which the expression cassette or polynucleotide of the invention is inserted may be any vector which may conveniently be subjected to recombinant DNA procedures, and the choice of the vector will often depend on the host cell into which it is to be introduced.

A vector according to the invention may be an autonomously replicating vector, i.e. a vector which exists as an extra-chromosomal entity, the replication of which is independent of chromosomal replication, e.g. a plasmid. Alternatively, the vector may be one which, when introduced into a host cell, is integrated into the host cell genome and replicated together with the chromosome (s) into which it has been integrated.

One type of vector is a "plasmid", which refers to a circular double stranded DNA loop into which additional DNA segments can be ligated. Another type of vector is a viral vector, wherein additional DNA segments can be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors are capable of directing the expression of genes to which they are operatively linked. Such vectors are referred to herein as "expression vectors". In general, expression vectors of utility in recombinant DNA techniques are often in the form of plasmids. The terms "plasmid" and "vector" can be used interchangeably herein as the plasmid is the most commonly used form of vector. However, the invention is intended to include such other forms of expression vectors, such as cosmid, viral vectors (e.g., replication defective retroviruses, adenoviruses and adeno-associated viruses) and phage vectors which serve equivalent functions.

For most filamentous fungi and yeast, the vector or expression construct is preferably integrated in the genome of the host cell in order to obtain stable transformants. However, for certain yeasts also suitable episomal vectors are available into which the expression construct can be incorporated for stable and high level expression, examples thereof include vectors derived from the 2μ and pKD1 plasmids of *Saccharomyces* and *Kluyveromyces*, respectively, or vectors containing an AMA sequence (e.g. AMA1 from *Aspergillus*). In case the expression constructs are integrated in the host cells genome, the constructs are either integrated at random loci in the genome, or at predetermined target loci using homologous recombination, in which case the target loci preferably comprise a highly expressed gene.

Accordingly, expression vectors useful in the present invention include chromosomal-, episomal- and virus-derived vectors e.g., vectors derived from bacterial plasmids, bacteriophage, yeast episome, yeast chromosomal elements, viruses such as baculoviruses, papova viruses, vaccinia viruses, adenoviruses, fowl pox viruses, pseudorabies viruses and retroviruses, and vectors derived from combinations thereof, such as those derived from plasmid and bacteriophage genetic elements, such as cosmids and phagemids.

Vectors according to the invention may be used in vitro, for example for the production of RNA or used to transfect or transform a host cell. The recombinant expression vector can be transcribed and translated in vitro, for example using T7 promoter regulatory sequences and T7 polymerase.

A vector of the invention may comprise two or more, for example three, four or five, polynucleotides of the invention, for example for overexpression.

The recombinant expression vectors of the invention comprise a nucleic acid of the invention in a form suitable for expression of the nucleic acid in a host cell, which means that the recombinant expression vector includes one or more regulatory sequences, selected on the basis of the host cells to be used for expression, which is operably linked to the nucleic acid sequence to be expressed.

Within a vector, such as an expression vector, "operably linked" is intended to mean that the nucleotide sequence of interest is linked to the regulatory sequence(s) in a manner which allows for expression of the nucleotide sequence (e.g., in an in vitro transcription/translation system or in a host cell when the vector is introduced into the host cell), i.e. the term "operably linked" refers to a juxtaposition wherein the components described are in a relationship permitting them to function in their intended manner. A regulatory sequence such as a promoter, enhancer or other expression regulation signal "operably linked" to a coding sequence is positioned in such a way that expression of the coding sequence is achieved under condition compatible with the control sequences or the sequences are arranged so that they function in concert for their intended purpose, for example transcription initiates at a promoter and proceeds through the DNA sequence encoding the polypeptide.

A vector or expression construct for a given host cell may thus comprise the following elements operably linked to each other in a consecutive order from the 5'-end to 3'-end relative to the coding strand of the sequence encoding the polypeptide of the first invention: (1) a promoter sequence capable of directing transcription of the nucleotide sequence encoding the polypeptide in the given host cell; (2) optionally, a signal sequence capable of directing secretion of the polypeptide from the given host cell into a culture medium; (3) a DNA sequence of the invention encoding a mature and preferably active form of a polypeptide having beta-glucosidase activity; and preferably also (4) a transcription termination region (terminator) capable of terminating transcription downstream of the nucleotide sequence encoding the polypeptide.

Downstream of the nucleotide sequence according to the invention there may be a 3' untranslated region containing one or more transcription termination sites (e.g. a terminator). The origin of the terminator is less critical. The terminator can, for example, be native to the DNA sequence encoding the polypeptide. However, preferably a yeast terminator is used in yeast host cells and a filamentous fungal terminator is used in filamentous fungal host cells. More preferably, the terminator is endogenous to the host cell (in which the nucleotide sequence encoding the polypeptide is to be expressed). In the transcribed region, a ribosome binding site for translation may be present. The coding portion of the mature transcripts expressed by the constructs will include a translation initiating AUG at the beginning and a termination codon appropriately positioned at the end of the polypeptide to be translated.

Enhanced expression of the polynucleotide of the invention may also be achieved by the selection of heterologous regulatory regions, e.g. promoter, secretion leader and/or terminator regions, which may serve to increase expression and, if desired, secretion levels of the polypeptide of interest from the expression host and/or to provide for the inducible control of the expression of a polypeptide of the invention.

It will be appreciated by those skilled in the art that the design of the expression vector can depend on such factors as the choice of the host cell to be transformed, the level of expression of polypeptide desired, etc. The vectors, such as expression vectors, of the invention can be introduced into host cells to thereby produce proteins or peptides, encoded by nucleic acids as described herein (e.g. TEMER06387 polypeptides, mutant forms of TEMER06387 polypeptides, fragments, variants or functional equivalents thereof. The vectors, such as recombinant expression vectors, of the invention can be designed for expression of TEMER06387 polypeptides in prokaryotic or eukaryotic cells.

For example, TEMER06387 polypeptides can be expressed in bacterial cells such as *E. coli*, insect cells (using baculovirus expression vectors), filamentous fungi, yeast cells or mammalian cells. Suitable host cells are discussed further in Goeddel, Gene Expression Technology: Methods in Enzymology 185, Academic Press, San Diego, Calif. (1990). Representative examples of appropriate hosts are described hereafter.

Appropriate culture mediums and conditions for the above-described host cells are known in the art.

The term "control sequences" or "regulatory sequences" is defined herein to include at least any component which may be necessary and/or advantageous for the expression of a polypeptide. Any control sequence may be native or foreign to the nucleic acid sequence of the invention encoding a polypeptide. Such control sequences may include, but are not limited to, a promoter, a leader, optimal translation initiation sequences (as described in Kozak, 1991, J. Biol. Chem. 266: 19867-19870), a secretion signal sequence, a pro-peptide sequence, a polyadenylation sequence, a transcription terminator. At a minimum, the control sequences typically include a promoter, and transcriptional and translational stop signals. As set out above, the term "operably linked" is defined herein as a configuration in which a control sequence is appropriately placed at a position relative to the coding sequence of the DNA sequence such that the control sequence directs the production of a polypeptide.

The control sequences may be provided with linkers for the purpose of introducing specific restriction sites facilitating ligation of the control sequences with the coding region of the nucleic acid sequence encoding a polypeptide. The term "operably linked" is defined herein as a configuration in which a control sequence is appropriately placed at a position relative to the coding sequence of the DNA sequence such that the control sequence directs the production of a polypeptide.

The control sequence may be an appropriate promoter sequence, a nucleic acid sequence, which is recognized by a host cell for expression of the nucleic acid sequence. The promoter sequence contains transcriptional control sequences, which mediate the expression of the polypeptide. The promoter may be any nucleic acid sequence, which shows transcriptional activity in the cell including mutant, truncated, and hybrid promoters, and may be obtained from genes encoding extracellular or intracellular polypeptides either homologous or heterologous to the cell.

The control sequence may also be a suitable transcription terminator sequence, a sequence recognized by a filamentous fungal cell to terminate transcription. The terminator sequence is operably linked to the 3' terminus of the nucleic acid sequence encoding the polypeptide. Any terminator, which is functional in the cell, may be used in the present invention.

The control sequence may also be a terminator. Preferred terminators for filamentous fungal cells are obtained from the genes encoding *A. oryzae* TAKA amylase, *A. niger* glucoamylase (glaA), *A. nidulans* anthranilate synthase, *A. niger* alpha-glucosidase, trpC gene and *Fusarium oxysporum* trypsin-like protease.

The control sequence may also be a suitable leader sequence, a non-translated region of a mRNA which is important for translation by the filamentous fungal cell. The leader sequence is operably linked to the 5' terminus of the nucleic acid sequence encoding the polypeptide. Any leader sequence, which is functional in the cell, may be used in the present invention. Preferred leaders for filamentous fungal cells are obtained from the genes encoding *A. oryzae* TAKA amylase and *A. nidulans* triose phosphate isomerase and *A. niger* glaA.

Other control sequences may be isolated from the *Penicillium* IPNS gene, or pcbC gene, the beta tubulin gene. All the control sequences cited in WO 01/21779 are herewith incorporated by reference.

The control sequence may also be a polyadenylation sequence, a sequence which is operably linked to the 3' terminus of the nucleic acid sequence and which, when transcribed, is recognized by the filamentous fungal cell as a signal to add polyadenosine residues to transcribed mRNA. Any polyadenylation sequence, which is functional in the cell, may be used in the present invention. Preferred polyadenylation sequences for filamentous fungal cells are obtained from the genes encoding *A. oryzae* TAKA amylase, *A. niger* glucoamylase, *A. nidulans* anthranilate synthase, *Fusarium oxysporum* trypsin-like protease and *A. niger* alpha-glucosidase.

When the polypeptide according to the invention is to be secreted from the host cell into the cultivation medium, an appropriate signal sequence can be added to the polypeptide in order to direct the de novo synthesized polypeptide to the secretion route of the host cell. The person skilled in the art knows to select an appropriate signal sequence for a specific host. The signal sequence may be native to the host cell, or may be foreign to the host cell. As an example, a signal sequence from a polypeptide native to the host cell can be used. Preferably, said native polypeptide is a highly secreted polypeptide, i.e. a polypeptide that is secreted in amounts higher than 10% of the total amount of polypeptide being secreted. The signal sequences preferably used according to the invention are for example: pmeA.

As an alternative for a signal sequence, the polypeptide of the invention can be fused to a secreted carrier polypeptide, or part thereof. Such chimeric construct is directed to the secretion route by means of the signal sequence of the carrier polypeptide, or part thereof. In addition, the carrier polypeptide will provide a stabilizing effect to the polypeptide according to the invention and or may enhance solubility. Such carrier polypeptide may be any polypeptide. Preferably, a highly secreted polypeptide is used as a carrier polypeptide. The carrier polypeptide may be native or foreign to the polypeptide according to the invention. The carrier polypeptide may be native of may be foreign to the host cell. Examples of such carrier polypeptides are glucoamylase, pre-pro sequence of alpha-Mating factor, cellulose binding domain of *Clostridium cellulovorans* cellulose binding protein A, glutathione S-transferase, chitin binding domain of *Bacillus circulans* chitinase A1, maltose binding domain encoded by the malE gene of *E. coli* K12, beta-galactosidase, and alkaline phosphatase. A preferred carrier polypeptide for expression of such chimeric construct in *Aspergillus* cells is glucoamylase. The carrier protein and polypeptide may contain a specific amino acid motif to facilitate isolation of the polypeptide; the polypeptide according to the invention may be released by a special releasing agent. The releasing agent may be a proteolytic enzyme or a chemical agent. An example of such amino acid motif is the KEX protease cleavage site, which is well-known to the person skilled in the art.

A signal sequence can be used to facilitate secretion and isolation of a protein or polypeptide of the invention. Signal sequences are typically characterized by a core of hydrophobic amino acids, which are generally cleaved from the mature protein during secretion in one or more cleavage events. Such signal peptides contain processing sites that allow cleavage of the signal sequence from the mature proteins as they pass through the secretory pathway. The signal sequence directs secretion of the protein, such as from a eukaryotic host into which the expression vector is transformed, and the signal sequence is subsequently or concurrently cleaved. The protein can then be readily purified from the extracellular medium by known methods. Alternatively, the signal sequence can be linked to the protein of interest using a sequence, which facilitates purification, such as with a GST domain. Thus, for instance, the sequence encoding the polypeptide may be fused to a marker sequence, such as a sequence encoding a peptide, which facilitates purification of the fused polypeptide. In certain preferred embodiments of this aspect of the invention, the marker sequence is a hexa-histidine peptide, such as the tag provided in a pQE vector (Qiagen, Inc.), among others, many of which are commercially available. As described in Gentz et al, Proc. Natl. Acad.

Sci. USA 86:821-824 (1989), for instance, hexa-histidine provides for convenient purification of the fusion protein. The HA tag is another peptide useful for purification which corresponds to an epitope derived of influenza hemaglutinin protein, which has been described by Wilson et al., Cell 37:767 (1984), for instance.

Preferably, a TEMER06387 fusion protein of the invention is produced by standard recombinant DNA techniques. For example, DNA fragments coding for the different polypeptide sequences are ligated together in-frame in accordance with conventional techniques, for example by employing blunt-ended or stagger-ended termini for ligation, restriction enzyme digestion to provide for appropriate termini, filling-in of cohesive ends as appropriate, alkaline phosphatase treatment to avoid undesirable joining, and enzymatic ligation. In another embodiment, the fusion gene can be synthesized by conventional techniques including automated DNA synthesizers. Alternatively, PCR amplification of gene fragments can be carried out using anchor primers, which give rise to complementary overhangs between two consecutive gene fragments which can subsequently be annealed and reamplified to generate a chimeric gene sequence (see, for example, Current Protocols in Molecular Biology, eds. Ausubel et al. John Wiley & Sons: 1992). Moreover, many expression vectors are commercially available that already encode a fusion moiety (e.g., a GST polypeptide). A TEMER06387-encoding nucleic acid can be cloned into such an expression vector such that the fusion moiety is linked in-frame to the TEMER06387 protein.

Preferably, the efficiency of targeted integration into the genome of the host cell, i.e. integration in a predetermined target locus, is increased by augmented homologous recombination abilities of the host cell. Such phenotype of the cell preferably involves a deficient hdfA or hdfB gene as described in WO2005/095624. WO2005/095624 discloses a preferred method to obtain a filamentous fungal cell comprising increased efficiency of targeted integration.

Optionally, the host cell comprises an elevated unfolded protein response (UPR) compared to the wild type cell to enhance production abilities of a polypeptide of interest. UPR may be increased by techniques described in US2004/0186070A1 and/or US2001/0034045A1 and/or WO01/72783A2 and/or WO2005/123763. More specifically, the protein level of HAC1 and/or IRE1 and/or PTC2 has been modulated, and/or the SEC61 protein has been engineered in order to obtain a host cell having an elevated UPR.

Alternatively, or in combination with an elevated UPR, the host cell is genetically modified to obtain a phenotype displaying lower protease expression and/or protease secretion compared to the wild-type cell in order to enhance production abilities of a polypeptide of interest. Such phenotype may be obtained by deletion and/or modification and/or inactivation of a transcriptional regulator of expression of proteases. Such a transcriptional regulator is e.g. prtT. Lowering expression of proteases by modulation of prtT may be performed by techniques described in US2004/0191864A1.

Alternatively, or in combination with an elevated UPR and/or a phenotype displaying lower protease expression and/or protease secretion, the host cell displays an oxalate deficient phenotype in order to enhance the yield of production of a polypeptide of interest. An oxalate deficient phenotype may be obtained by techniques described in WO2004/070022A2.

Alternatively, or in combination with an elevated UPR and/or a phenotype displaying lower protease expression and/or protease secretion and/or oxalate deficiency, the host cell displays a combination of phenotypic differences compared to the wild cell to enhance the yield of production of the polypeptide of interest. These differences may include, but are not limited to, lowered expression of glucoamylase and/or neutral alpha-amylase A and/or neutral alpha-amylase B, protease, and oxalic acid hydrolase. Said phenotypic differences displayed by the host cell may be obtained by genetic modification according to the techniques described in US2004/0191864A1.

Alternatively, or in combination with an elevated UPR and/or a phenotype displaying lower protease expression and/or protease secretion and/or oxalate deficiency and a combination of phenotypic differences compared to the wild cell to enhance the yield of production of the polypeptide of interest, the host cell displays a deficiency in toxin genes, disabling the ability of the filamentous fungal host cell to express toxins. Such toxins include, but are not limited to, ochratoxins, fumonisins, cyclapiazonic acid, 3-nitropropionic acid, emodin, malformin, aflatoxins and secalonic acids. Such deficiency is preferably such as described in WO2000/039322.

(Over)Expression

In a preferred embodiment, the polynucleotides of the present invention as described herein may be over-expressed in a microbial strain of the invention compared to the parent microbial strain in which said gene is not over-expressed. Over-expression of a polynucleotide sequence is defined herein as the expression of the said sequence gene which results in an activity of the enzyme encoded by the said sequence in a microbial strain being at least about 1.5-fold the activity of the enzyme in the parent microbial; preferably the activity of said enzyme is at least about 2-fold, more preferably at least about 3-fold, more preferably at least about 4-fold, more preferably at least about 5-fold, even more preferably at least about 10-fold and most preferably at least about 20-fold the activity of the enzyme in the parent microbial.

The vector may further include sequences flanking the polynucleotide giving rise to RNA which comprise sequences homologous to eukaryotic genomic sequences or viral genomic sequences. This will allow the introduction of the polynucleotides of the invention into the genome of a host cell.

An integrative cloning vector may integrate at random or at a predetermined target locus in the chromosome(s) of the host cell into which it is to be integrated. In a preferred embodiment of the invention, an integrative cloning vector may comprise a DNA fragment which is homologous to a DNA sequence in a predetermined target locus in the genome of host cell for targeting the integration of the cloning vector to this predetermined locus. In order to promote targeted integration, the cloning vector may be preferably linearized prior to transformation of the host cell. Linearization may preferably be performed such that at least one but preferably either end of the cloning vector is flanked by sequences homologous to the target locus. The length of the homologous sequences flanking the target locus is preferably at least about 0.1 kb, such as about at least 0.2 kb, more preferably at least about 0.5 kb, even more preferably at least about 1 kb, most preferably at least about 2 kb. Preferably, the parent host strains may be modified for improved frequency of targeted DNA integration as described in WO05/095624 and/or WO2007/115886.

The deletion example provided in the present invention, uses the promoter of the gene as 5'-flank and the gene as the 3'-flank to insert a selection marker between the promoter and gene, thereby disturbing (i.e. functionally inactivating) gene transcription. The gene sequences given above can be used to make similar functionally inactivated genes. The genes may be split in two, yielding a 5'-flank and a 3'-flank, but the gene may also be used to clone a larger piece of genomic DNA containing the promoter and terminator regions of the gene, which than can function as 5'-flank and a 3'-flanks.

The vector system may be a single vector, such as a single plasmid, or two or more vectors, such as two or more plasmids, which together contain the total DNA to be introduced into the genome of the host cell.

The vector may contain a polynucleotide of the invention oriented in an antisense direction to provide for the production of antisense RNA.

Vector DNA can be introduced into prokaryotic or eukaryotic cells via conventional transformation or transfection techniques. As used herein, the terms "transformation" and "transfection" are intended to refer to a variety of art-recognized techniques for introducing foreign nucleic acid (e.g., DNA) into a host cell, including calcium phosphate or calcium chloride co-precipitation, DEAE-dextran-mediated transfection, transduction, infection, lipofection, cationic lipidmediated transfection or electroporation. Suitable methods for transforming or transfecting host cells can be found in Sambrook, et al. (Molecular Cloning: A Laboratory Manual, $2^{nd}$, ed. Cold Spring Harbor Laboratory, Cold Spring Harbor Laboratory Press, Cold Spring Harbor, N.Y., 1989), Davis et al., Basic Methods in Molecular Biology (1986) and other laboratory manuals.

For stable transfection of mammalian cells, it is known that, depending upon the expression vector and transfection technique used, only a small fraction of cells may integrate the foreign DNA into their genome. In order to identify and select these integrants, a gene that encodes a selectable marker (e.g., resistance to antibiotics) is generally introduced into the host cells along with the gene of interest. Preferred selectable markers include, but are not limited to, those which confer resistance to drugs or which complement a defect in the host cell. They include e.g. versatile marker genes that can be used for transformation of most filamentous fungi and yeasts such as acetamidase genes or cDNAs (the amdS, niaD, facA genes or cDNAs from *A. nidulans, A. oryzae* or *A. niger*), or genes providing resistance to antibiotics like G418, hygromycin, bleomycin, kanamycin, methotrexate, phleomycin orbenomyl resistance (benA). Alternatively, specific selection markers can be used such as auxotrophic markers which require corresponding mutant host strains: e.g. URA3 (from *S. cerevisiae* or analogous genes from other yeasts), pyrG or pyrA (from *A. nidulans* or *A. niger*), argB (from *A. nidulans* or *A. niger*) or trpC. In a preferred embodiment the selection marker is deleted from the transformed host cell after introduction of the expression construct so as to obtain transformed host cells capable of producing the polypeptide which are free of selection marker genes.

Other markers include ATP synthetase, subunit 9 (oliC), orotidine-5'-phosphatedecarboxylase (pvrA), the bacterial G418 resistance gene (this may also be used in yeast, but not in fungi), the ampicillin resistance gene (*E. coli*), the neomycin resistance gene (*Bacillus*), the nourseothricine resistance gene nat1 from *Streptomyces nursei*, the pyrithiamine resistance gene ptrA of *Aspergillus oryzae* and the *E. coli* uidA gene, coding for β-glucuronidase (GUS). Vectors may be used in vitro, for example for the production of RNA or used to transfect or transform a host cell.

Expression of proteins in prokaryotes is often carried out in *E. coli* with vectors containing constitutive or inducible promoters directing the expression of either fusion or non-fusion proteins. Fusion vectors add a number of amino acids to a protein encoded therein, e.g. to the amino terminus of the recombinant protein. Such fusion vectors typically serve three purposes: 1) to increase expression of recombinant protein; 2) to increase the solubility of the recombinant protein; and 3) to aid in the purification of the recombinant protein by acting as a ligand in affinity purification. Often, in fusion expression vectors, a proteolytic cleavage site is introduced at the junction of the fusion moiety and the recombinant protein to enable separation of the recombinant protein from the fusion moiety subsequent to purification of the fusion protein.

As indicated, the expression vectors will preferably contain selectable markers. Such markers include dihydrofolate reductase or neomycin resistance for eukaryotic cell culture and tetracyline or ampicillin resistance for culturing in *E. coli* and other bacteria.

Vectors preferred for use in bacteria are for example disclosed in WO-A1-2004/074468, which are hereby enclosed by reference. Other suitable vectors will be readily apparent to the skilled artisan.

For secretion of the translated protein into the lumen of the endoplasmic reticulum, into the periplasmic space or into the extracellular environment, appropriate secretation signal may be incorporated into the expressed polypeptide. The signals may be endogenous to the polypeptide or they may be heterologous signals.

The TEMER06387 polypeptide may be expressed in a modified form, such as a fusion protein, and may include not only secretion signals but also additional heterologous functional regions. Thus, for instance, a region of additional amino acids, particularly charged amino acids, may be added to the N-terminus of the polypeptide to improve stability and persistence in the host cell, during purification or during subsequent handling and storage. Also, peptide moieties may be added to the polypeptide to facilitate purification The invention provides an isolated polypeptide having the amino acid sequence according to SEQ ID NO: 2, and an amino acid sequence obtainable by expressing the polynucleotide of SEQ ID NO: 1 in an appropriate host. Also, a peptide or polypeptide comprising a variant of the above polypeptides, such as a functional equivalent, is comprised within the present invention. The above polypeptides are collectively comprised in the term "polypeptides according to the invention"

The term "variant peptide" or "variant polypeptide" is defined herein as a peptide or polypeptide, respectively, comprising one or more alterations, such as substitutions, insertions, deletions and/or truncations of one or more specific amino acid residues at one or more specific positions in the peptide or polypeptide, respectively. Accordingly, a variant signal peptide is a signal peptide comprising one or more alterations, such as substitutions, insertions, deletions and/or truncations of one or more specific amino acid residues at one or more specific positions in the signal peptide.

The term "polynucleotide" is identical to the term "nucleic acid molecule" and can herein be read interchangeably. The term refers to a polynucleotide molecule, which is a ribonucleic acid (RNA) or deoxyribonucleic acid (DNA) molecule, either single stranded or double stranded. A polynucleotide may either be present in isolated form, or be comprised in recombinant nucleic acid molecules or vectors, or be comprised in a host cell.

The term "variant polynucleotide" is defined herein as a polynucleotide comprising one or more alterations, such as substitutions, insertions, deletions and/or truncations of one or more nucleotides at one or more specific positions in the polynucleotide.

The terms "peptide" and "oligopeptide" are considered synonymous (as is commonly recognized) and each term can be used interchangeably, as the context requires, to indicate a chain of at least two amino acids coupled by peptidyl linkages. The word "polypeptide" is used herein for chains containing more than seven amino acid residues. All oligopeptide and polypeptide formulas or sequences herein are written from left to right and in the direction from amino terminus to carboxy terminus. The one-letter code of amino acids used herein is commonly known in the art and can be found in Sambrook, et al. (Molecular Cloning: A Laboratory Manual, $2^{nd}$, ed. Cold Spring Harbor Laboratory, Cold Spring Harbor Laboratory Press, Cold Spring Harbor, N.Y., 1989).

By "isolated" polypeptide or protein is intended a polypeptide or protein removed from its native environment. For example, recombinantly produced polypeptides and proteins expressed in host cells are considered isolated for the purpose of the invention as are native or recombinant polypeptides which have been substantially purified by any suitable technique such as, for example, the single-step purification method disclosed in Smith and Johnson, Gene 67:31-40 (1988).

The TEMER06387 beta-glucosidase polypeptide according to the invention can be recovered and purified from recombinant cell cultures by methods known in the art. Most preferably, high performance liquid chromatography ("HPLC") is employed for purification.

Polypeptides of the present invention include naturally purified products, products of chemical synthetic procedures, and products produced by recombinant techniques from a prokaryotic or eukaryotic host, including, for example, bacterial, yeast, higher plant, insect and mammalian cells. Depending upon the host employed in a recombinant production procedure, the polypeptides of the present invention may be glycosylated or may be non-glycosylated. In addition, polypeptides of the invention may also include an initial modified methionine residue, in some cases as a result of host-mediated processes.

The invention also features biologically active fragments of the polypeptides according to the invention.

Biologically active fragments of a polypeptide of the invention include polypeptides comprising amino acid sequences sufficiently identical to or derived from the amino acid sequence of the TEMER06387 polypeptide (e.g., the amino acid sequence of SEQ ID NO: 2), which include fewer amino acids than the full length polypeptide but which exhibit at least one biological activity of the corresponding full-length polypeptide. Typically, biologically active fragments comprise a domain or motif with at least one activity of the TEMER06387 polypeptide.

A biologically active fragment of a polypeptide of the invention can be a polypeptide which is, for example, about 10, about 25, about 50, about 100 or more amino acids in length or at least about 100 amino acids, at least 150, 200, 250, 300, 350, 400 amino acids in length, or of a length up the total number of amino acids of polypeptide of the invention.

Moreover, other biologically active portions, in which other regions of the polypeptide are deleted, can be prepared by recombinant techniques and evaluated for one or more of the biological activities of the native form of a polypeptide of the invention.

The invention also features nucleic acid fragments which encode the above biologically active fragments of the TEMER06387 polypeptide.

Polypeptides

In another aspect of the invention, improved TEMER06387 polypeptides are provided. Improved TEMER06387 polypeptides are polypeptides wherein at least one biological activity is improved. Such polypeptides may be obtained by randomly introducing mutations along all or part of the TEMER06387 coding sequence, such as by saturation mutagenesis, and the resulting mutants can be expressed recombinantly and screened for biological activity.

Improved variants of the amino acid sequences of the present invention leading to an improved beta-glucosidase function may be obtained by the corresponding genes of the present invention. Among such modifications are included:
1. Error prone PCR to introduce random mutations, followed by a screening of obtained variants and isolating of variants with improved kinetic properties
2. Family shuffling of related variants of the genes encoding the beta-glucosidase enzyme, followed by a screening of obtained variants and isolating of variants with improved kinetic properties Variants of the genes of the present invention leading to an increased level of mRNA and/or polypeptide, resulting in more beta-glucosidase activity may be obtained by the polynucleotide sequences of said genes. Among such modifications are included:
1. Improving the codon usage in such a way that the codons are (optimally) adapted to the parent microbial host.
2. Improving the codon pair usage in such a way that the codons are (optimally) adapted to the parent microbial host
3. Addition of stabilizing sequences to the genomic information encoding the beta-glucosidase polypeptide resulting in mRNA molecules with an increased half life Preferred methods to isolate variants with improved catalytic properties or increased levels of mRNA or polypeptide are described in WO03/010183 and WO03/01311. Preferred methods to optimize the codon usage in parent microbial strains are described in PCT/EP2007/05594. Preferred methods for the addition of stabilizing elements to the genes encoding the beta-glucosidase polypeptide of the invention are described in WO2005/059149.

In a preferred embodiment the TEMER06387 polypeptide has an amino acid sequence according to SEQ ID NO: 2. In another embodiment, the TEMER06387 polypeptide is substantially homologous to the amino acid sequence according to SEQ ID NO: 2 and retains at least one biological activity of a polypeptide according to SEQ ID NO: 2, yet differs in amino acid sequence due to natural variation or mutagenesis as described.

In a further preferred embodiment, the TEMER06387 polypeptide has an amino acid sequence encoded by an isolated nucleic acid fragment capable of hybridizing to a nucleic acid according to SEQ ID NO: 1, preferably under highly stringent hybridization conditions.

Accordingly, the TEMER06387 polypeptide is preferably a polypeptide which comprises an amino acid sequence at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 96%, at least 97%, at least 98%, at least 99% or more homologous to the amino acid sequence shown in SEQ ID NO: 2 and, typically, retains at least one functional activity of the polypeptide according to SEQ ID NO: 2.

Functional equivalents of a polypeptide according to the invention can also be identified e.g. by screening combinatorial libraries of mutants, e.g. truncation mutants, of the polypeptide of the invention for beta-glucosidase activity. In one embodiment, a variegated library of variants is generated by combinatorial mutagenesis at the nucleic acid level. A variegated library of variants can be produced by, for example, enzymatically ligating a mixture of synthetic oligonucleotides into gene sequences such that a degenerate set of potential polypeptide sequences is expressible as individual polypeptides, or alternatively, as a set of larger fusion proteins (e.g. for phage display). There are a variety of methods that can be used to produce libraries of potential variants of the polypeptides of the invention from a degenerate oligonucleotide sequence. Methods for synthesizing degenerate oligonucleotides are known in the art (see, e.g., Narang (1983) Tetrahedron 39:3; Itakura et al. (1984) Annu. Rev. Biochem. 53:323; Itakura et al. (1984) Science 198:1056; Ike et al. (1983) Nucleic Acid Res. 11:477).

In addition, libraries of fragments of the coding sequence of a polypeptide of the invention can be used to generate a variegated population of polypeptides for screening a subsequent selection of variants. For example, a library of coding sequence fragments can be generated by treating a double stranded PCR fragment of the coding sequence of interest with a nuclease under conditions wherein nicking occurs only about once per molecule, denaturing the double stranded DNA, renaturing the DNA to form double stranded DNA which can include sense/antisense pairs from different nicked products, removing single stranded portions from reformed duplexes by treatment with 51 nuclease, and ligating the resulting fragment library into an expression vector. By this method, an expression library can be derived which encodes N-terminal and internal fragments of various sizes of the protein of interest.

Several techniques are known in the art for screening gene products of combinatorial libraries made by point mutations of truncation, and for screening cDNA libraries for gene products having a selected property. The most widely used techniques, which are amenable to high through-put analysis, for screening large gene libraries typically include cloning the gene library into replicable expression vectors, transforming appropriate cells with the resulting library of vectors, and expressing the combinatorial genes under conditions in which detection of a desired activity facilitates isolation of the vector encoding the gene whose product was detected. Recursive ensemble mutagenesis (REM), a technique which enhances the frequency of functional mutants in the libraries, can be used in combination with the screening assays to identify variants of a polypeptide of the invention (Arkin and Yourvan (1992) Proc. Natl. Acad. Sci. USA 89:7811-7815; Delgrave et al. (1993) Protein Engineering 6(3): 327-331).

In addition to the TEMER06387 gene sequence shown in SEQ ID NO: 1, it will be apparent for the person skilled in the art that DNA sequence polymorphisms may exist within a given population, which may lead to changes in the amino acid sequence of the TEMER06387 polypeptide. Such genetic polymorphisms may exist in cells from different populations or within a population due to natural allelic variation. Allelic variants may also include functional equivalents.

Fragments of a polynucleotide according to the invention may also comprise polynucleotides not encoding functional polypeptides. Such polynucleotides may function as probes or primers for a PCR reaction.

Nucleic acids according to the invention irrespective of whether they encode functional or non-functional polypeptides can be used as hybridization probes or polymerase chain reaction (PCR) primers. Uses of the nucleic acid molecules of the present invention that do not encode a polypeptide having a TEMER06387 activity include, inter alia, (1) isolating the gene encoding the TEMER06387 polypeptide, or allelic variants thereof from a cDNA library e.g. from suitable microorganisms; (2) in situ hybridization (e.g. FISH) to metaphase chromosomal spreads to provide precise chromosomal location of the TEMER06387 gene as described in Verma et al., Human Chromosomes: a Manual of Basic Techniques, Pergamon Press, New York (1988); (3) Northern blot analysis for detecting expression of TEMER06387 mRNA in specific tissues and/or cells and 4) probes and primers that can be used as a diagnostic tool to analyse the presence of a nucleic acid hybridizable to the TEMER06387 probe in a given biological (e.g. tissue) sample.

Also encompassed by the invention is a method of obtaining a functional equivalent of a TEMER06387 gene. Such a method entails obtaining a labelled probe that includes an isolated nucleic acid which encodes all or a portion of the polypeptide sequence according to SEQ ID NO: 2 or a variant thereof; screening a nucleic acid fragment library with the labelled probe under conditions that allow hybridization of the probe to nucleic acid fragments in the library, thereby forming nucleic acid duplexes, and preparing a full-length gene sequence from the nucleic acid fragments in any labelled duplex to obtain a gene related to the TEMER06387 gene.

In one embodiment, a TEMER06387 nucleic acid of the invention is at least 70%, at least 71%, at least 72%, at least 73%, at least 74%, at least 75%, at least 76%, at least 77%, at least 78%, at least 79%, least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or more homologous to a nucleic acid sequence shown in SEQ ID NO: 1 or the complement thereof.

Further provided are: host cells comprising a polynucleotide or vector of the invention. The polynucleotide may be heterologous to the genome of the host cell. The term "heterologous", usually with respect to the host cell, means that the polynucleotide does not naturally occur in the genome of the host cell or that the polypeptide is not naturally produced by that cell.

In another embodiment, the invention features cells, e.g., transformed host cells or recombinant host cells that contain a nucleic acid encompassed by the invention. A "transformed cell" or "recombinant cell" is a cell into which (or into an ancestor of which) has been introduced, by means of recombinant DNA techniques, a nucleic acid according to the invention. Both prokaryotic and eukaryotic cells are included, e.g., bacteria, fungi, yeast, and the like, especially preferred are cells from filamentous fungi, such as *Aspergillus niger* or *Talaromyces emersonii*.

A host cell can be chosen that modulates the expression of the inserted sequences, or modifies and processes the gene product in a specific, desired fashion. Such modifications (e.g., glycosylation) and processing (e.g., cleavage) of protein products may facilitate optimal functioning of the protein.

Various host cells have characteristic and specific mechanisms for post-translational processing and modification of proteins and gene products. Appropriate cell lines or host systems familiar to those of skill in the art of molecular biology and/or microbiology can be chosen to ensure the desired and correct modification and processing of the foreign protein expressed. To this end, eukaryotic host cells that possess the cellular machinery for proper processing of the primary transcript, glycosylation, and phosphorylation of the gene product can be used. Such host cells are well known in the art.

If desired, a cell as described above may be used to in the preparation of a polypeptide according to the invention. Such a method typically comprises cultivating a host cell (e.g. transformed or transfected with an expression vector as described above) under conditions to provide for expression (by the vector) of a coding sequence encoding the polypeptide, and optionally recovering the expressed polypeptide. Polynucleotides of the invention can be incorporated into a recombinant replicable vector, e.g. an expression vector. The vector may be used to replicate the nucleic acid in a compatible host cell. Thus in a further embodiment, the invention provides a method of making a polynucleotide of the invention by introducing a polynucleotide of the invention into a replicable vector, introducing the vector into a compatible host cell, and growing the host cell under conditions which bring about the replication of the vector. The vector may be recovered from the host cell.

Preferably the polypeptide is produced as a secreted protein in which case the nucleotide sequence encoding a mature form of the polypeptide in the expression construct is operably linked to a nucleotide sequence encoding a signal sequence. Preferably the signal sequence is native (homologous) to the nucleotide sequence encoding the polypeptide. Alternatively the signal sequence is foreign (heterologous) to the nucleotide sequence encoding the polypeptide, in which case the signal sequence is preferably endogenous to the host cell in which the nucleotide sequence according to the invention is expressed. Examples of suitable signal sequences for yeast host cells are the signal sequences derived from yeast a-factor genes. Similarly, a suitable signal sequence for filamentous fungal host cells is e.g. a signal sequence derived from a filamentous fungal amyloglucosidase (AG) gene, e.g. the *A. niger* glaA gene. This may be used in combination with the amyloglucosidase (also called (gluco) amylase) promoter itself, as well as in combination with other promoters. Hybrid signal sequences may also be used with the context of the present invention.

Preferred heterologous secretion leader sequences are those originating from the fungal amyloglucosidase (AG) gene (glaA-both 18 and 24 amino acid versions e.g. from *Aspergillus*), the α-factor gene (yeasts e.g. *Saccharomyces* and *Kluyveromyces*) or the α-amylase gene (*Bacillus*).

The vectors may be transformed or transfected into a suitable host cell as described above to provide for expression of a polypeptide of the invention. This process may comprise culturing a host cell transformed with an expression vector as described above under conditions to provide for expression by the vector of a coding sequence encoding the polypeptide.

Host Cells

The invention thus provides host cells transformed or transfected with or comprising a polynucleotide or vector of the invention. Preferably the polynucleotide is carried in a vector for the replication and expression of the polynucleotide. The cells will be chosen to be compatible with the said vector and may for example be prokaryotic (for example bacterial), fungal, yeast or plant cells.

A heterologous host may also be chosen wherein the polypeptide of the invention is produced in a form which is substantially free from other cellulose-degrading or hemicellulose degrading enzymes. This may be achieved by choosing a host which does not normally produce such enzymes.

The invention encompasses processes for the production of the polypeptide of the invention by means of recombinant expression of a DNA sequence encoding the polypeptide. For this purpose the DNA sequence of the invention can be used for gene amplification and/or exchange of expression signals, such as promoters, secretion signal sequences, in order to allow economic production of the polypeptide in a suitable homologous or heterologous host cell. A homologous host cell is a host cell which is of the same species or which is a variant within the same species as the species from which the DNA sequence is derived.

Suitable host cells are preferably prokaryotic microorganisms such as bacteria, or more preferably eukaryotic organisms, for example fungi, such as yeasts or filamentous fungi, or plant cells. In general, yeast cells are preferred over fungal cells because they are easier to manipulate. However, some proteins are either poorly secreted from yeasts, or in some cases are not processed properly (e.g. hyperglycosylation in yeast). In these instances, a fungal host organism should be selected.

The host cell may over-express the polypeptide, and techniques for engineering over-expression are well known. The host may thus have two or more copies of the encoding polynucleotide (and the vector may thus have two or more copies accordingly).

Bacteria from the genus *Bacillus* are very suitable as heterologous hosts because of their capability to secrete proteins into the culture medium. Other bacteria suitable as hosts are those from the genera *Streptomyces* and *Pseudomonas*. A preferred yeast host cell for the expression of the DNA sequence encoding the polypeptide is of the genera *Saccharomyces, Kluyveromyces, Hansenula, Pichia, Yarrowia*, and *Schizosaccharomyces*.

More preferably a yeast host cell is selected from the group consisting of the species *Saccharomyces cerevisiae, Kluyveromyces lactis* (also known as *Kluyveromyces marxianus* var. *lactis*), *Hansenula polymorpha, Pichia pastoris, Yarrowia lipolytica* and *Schizosaccharomyces pombe*.

Most preferred are, however, (e.g. filamentous) fungal host cells. Preferred filamentous fungal host cells are selected from the group consisting of the genera *Aspergillus, Trichoderma/Hypocrea, Fusarium, Disporotrichum, Penicillium, Acremonium, Neurospora, Thermoascus, Myceliophtora, Sporotrichum, Thielavia, Chryosporium, Fusarium, Humicola, Neurospora* and *Talaromyces*.

More preferably a filamentous fungal host cell is of the species that include, but are not limited to *Aspergillus niger, Aspergillus awamori, Aspergillus tubingensis, Aspergillus aculeatus, Aspergillus foetidus, Aspergillus nidulans, Aspergillus japonicus, Aspergillus oryzae* and *Aspergillus ficuum, Trichoderma reesei/Hypocrea jecorina, Fusarium graminearum, Talaromyces emersonii, Penicillium decumbens, Acremonium alabamense, Neurospora crassa, Myceliophtora thernaophilurri, Sporotrichum cellulophilum, Disporotrichum dimorphosporum, Talaromyces emersonii, Talaromyces stipitatus* and *Thielavia terrestris*.

Host cells according to the invention include plant cells, and the invention therefore extends to transgenic organisms, such as plants and parts thereof, which contain one or more cells of the invention. The cells may heterologously express the polypeptide of the invention or may heterologously contain one or more of the polynucleotides of the invention. The transgenic (or genetically modified) plant may therefore have inserted (e.g. stably) into its genome a sequence encoding one or more of the polypeptides of the invention. The transformation of plant cells can be performed using known techniques, for example using a Ti or a Ri plasmid from Agrobacterium tumefaciens. The plasmid (or vector) may thus contain sequences necessary to infect a plant, and derivatives of the Tiand/or Ri plasmids may be employed.

Alternatively direct infection of a part of a plant, such as a leaf, root or stem can be effected. In this technique the plant to be infected can be wounded, for example by cutting the plant with a razor or puncturing the plant with a needle or rubbing the plant with an abrasive. The wound is then inoculated with the Agrobacterium. The plant or plant part can then be grown on a suitable culture medium and allowed to develop into a mature plant. Regeneration of transformed cells into genetically modified plants can be achieved by using known techniques, for example by selecting transformed shoots using an antibiotic and by sub-culturing the shoots on a medium containing the appropriate nutrients, plant hormones and the like.

The invention also includes cells that have been modified to express the beta-glucosidase polypeptide of the invention or a variant thereof. Such cells include transient, or preferably stable higher eukaryotic cell lines, such as mammalian cells or insect cells, lower eukaryotic cells, such as yeast and (e.g. filamentous) fungal cells or prokaryotic cells such as bacterial cells.

It is also possible for the polypeptides of the invention to be transiently expressed in a cell line or on a membrane, such as for example in a baculovirus expression system. Such systems, which are adapted to express the polypeptides according to the invention, are also included within the scope of the present invention.

According to the present invention, the production of the polypeptide of the invention can be effected by the culturing of microbial expression hosts, which have been transformed with one or more polynucleotides of the present invention, in a conventional nutrient fermentation medium.

Polypeptide/Enzyme Production

The recombinant host cells according to the invention may be cultured using procedures known in the art. For each combination of a promoter and a host cell, culture conditions are available which are conducive to the expression the DNA sequence encoding the polypeptide. After reaching the desired cell density or titre of the polypeptide the culture is stopped and the polypeptide is recovered using known procedures.

The fermentation medium can comprise a known culture medium containing a carbon source (e.g. glucose, maltose, molasses, starch, cellulose, xylan, pectin, lignocellulytic biomass hydrolysate, etc.), a nitrogen source (e.g. ammonium sulphate, ammonium nitrate, ammonium chloride, etc.), an organic nitrogen source (e.g. yeast extract, malt extract, peptone, etc.) and inorganic nutrient sources (e.g. phosphate, magnesium, potassium, zinc, iron, etc.). Optionally, an inducer (e.g. cellulose, pectin, xylan, maltose, maltodextrin or xylogalacturonan) may be included.

The selection of the appropriate medium may be based on the choice of expression host and/or based on the regulatory requirements of the expression construct. Such media are known to those skilled in the art. The medium may, if desired, contain additional components favouring the transformed expression hosts over other potentially contaminating microorganisms.

The production of polypeptide by the transformed host (fermentation) can be performed according to any known procedure. The production time may extend over a period of from about 0.5 to about 30 days. It may be a batch, continuous or fed-batch process, suitably at a temperature in the range of 0-100° C. or 0-80° C., for example, from about 0 to about 60° C. and/or at a pH, for example, from about 2 to about 10, or from about 3 to about 9. Preferred fermentation conditions are a temperature in the range of from about 20 to about 55° C. and/or at a pH of from about 3 to about 5. The appropriate conditions are usually selected based on the choice of the expression host and the polypeptide to be expressed.

After fermentation, if necessary, the cells can be removed from the fermentation broth by means of centrifugation or filtration. After fermentation has stopped or after removal of the cells, the polypeptide of the invention may then be recovered and, if desired, purified and isolated by conventional means.

Polypeptide/Enzyme Compositions

The invention provides a composition comprising a polypeptide of the invention and a cellulase and/or a hemicellulase and/or a pectinase.

When the polypeptide of the invention is a cellulase, a composition of the invention will typically comprise a hemicellulase and/or a pectinase in addition to the polypeptide of the invention.

When the polypeptide of the invention is a hemicellulase, a composition of the invention will typically comprise a cellulase and/or a pectinase in addition to the polypeptide of the invention.

When the polypeptide of the invention is a pectinase, a composition of the invention will typically comprise a cellulase and/or a hemicellulase in addition to the polypeptide of the invention.

A composition of the invention may comprise one, two or three or more classes of cellulase, for example one, two or all of an endo-1,4-β-glucanase (EG), an exo-cellobiohydrolase (CBH) and a β-glucosidase (BG).

A composition of the invention may comprise a polypeptide which has the same enzymatic activity, for example the same type of cellulase, hemicellulase and/or pectinase activity as that provided by a polypeptide of the invention.

A composition of the invention may comprise a polypeptide which has a different type of cellulase activity and/or hemicellulase activity and/or pectinase activity than that provided by a polypeptide of the invention. For example, a composition of the invention may comprise one type of cellulase and/or hemicellulase activity and/or pectinase activity provided by a polypeptide of the invention and a second type of cellulase and/or hemicellulase activity and/or pectinase activity provided by an additional hemicellulase/pectinase.

Herein, a cellulase is any polypeptide which is capable of degrading or cellulose. A polypeptide which is capable of degrading cellulose is one which is capable of catalysing the process of breaking down cellulose into smaller units, either partially, for example into cellodextrins, or completely into glucose monomers. A cellulase according to the invention may give rise to a mixed population of cellodextrins and glucose monomers when contacted with the cellulase. Such degradation will typically take place by way of a hydrolysis reaction.

Herein, a hemicellulase is any polypeptide which is capable of degrading or hemicellulose. That is to say, a hemicellulase may be capable of degrading or one or more of xylan, glucuronoxylan, arabinoxylan, glucomannan and xyloglucan. A polypeptide which is capable of degrading a hemicellulose is one which is capable of catalysing the process of breaking down the hemicellulose into smaller polysaccharides, either partially, for example into oligosaccharides, or completely into sugar monomers, for example hexose or pentose sugar monomers. A hemicellulase according to the invention may give rise to a mixed population of oligosaccharides and sugar monomers when contacted with the hemicellulase. Such degradation will typically take place by way of a hydrolysis reaction.

Herein, a pectinase is any polypeptide which is capable of degrading or pectin. A polypeptide which is capable of degrading pectin is one which is capable of catalysing the process of breaking down pectin into smaller units, either partially, for example into oligosaccharides, or completely into sugar monomers. A pectinase according to the invention may give rise to a mixed population of oligosacchardies and sugar monomers when contacted with the pectinase. Such degradation will typically take place by way of a hydrolysis reaction.

Accordingly, a composition of the invention may comprise any cellulase, for example, a cellobiohydrolase, an endo-β-1,4-glucanase, a β-glucosidase or a β-(1,3)(1,4)-glucanase.

Herein, a cellobiohydrolase is any polypeptide which is capable of catalysing the hydrolysis of 1,4-β-D-glucosidic linkages in cellulose or cellotetraose, releasing cellobiose from the ends of the chains. This enzyme may also be referred to as cellulase 1,4-β-cellobiosidase, 1,4-β-cellobiohydrolase, 1,4-β-D-glucan cellobiohydrolase, avicelase, exo-1,4-β-D-glucanase, exo-glucanase or exoglucanase. It may have the EC code EC 3.2.1.91. Cellobiohydrolases may be subdivided into cellobiohydrolase I (CBH I) and cellobiohydrolase II (CBH II). CBH I is defined as cellobiohydrolases that hydrolyse cellulose predominantly from the reducing ends, splitting off cellobiose. CBH II is defined as cellobiohydrolases that hydrolyse cellulose from predominantly from the non-reducing ends, splitting off cellobiose.

Herein, an endo-β-1,4-glucanase (EC 3.2.1.4) is any polypeptide which is capable of catalysing the endohydrolysis of 1,4-β-D-glucosidic linkages in cellulose, lichenin or cereal β-D-glucans. Such a polypeptide may also be capable of hydrolyzing 1,4-linkages in β-D-glucans also containing 1,3-linkages. This enzyme may also be referred to as cellulase, avicelase, β-1,4-endoglucan hydrolase, β-1,4-glucanase, carboxymethyl cellulase, celludextrinase, endo-1,4-β-D-glucanase, endo-1,4-β-D-glucanohydrolase, endo-1,4-β-glucanase or endoglucanase. CEA is herein an endoglucanase EC 3.2.1.4 that based on its 3D structure is classified under Glycosyl Hydrolase family 5 (GH5). Known activities for members of family GH5 include chitosanase (EC 3.2.1.132); β-mannosidase (EC 3.2.1.25); Cellulase (EC 3.2.1.4); glucan 1,3-β-glucosidase (EC 3.2.1.58); licheninase (EC 3.2.1.73); glucan endo-1,6-β-glucosidase (EC 3.2.1.75); mannan endo-β-1,4-mannosidase (EC 3.2.1.78); endo-β-1,4-xylanase (EC 3.2.1.8); cellulose β-1,4-cellobiosidase (EC 3.2.1.91); endo-β-1,6-galactanase (EC 3.2.1.-); β-1,3-mannanase (EC 3.2.1.-); xyloglucan-specific endo-β-1,4-glucanase (EC 3.2.1.151); mannan transglycosylase (EC 2.4.1.-). CEB is herein an endoglucanase EC 3.2.1.4 that based on its 3D structure is classified under Glycosyl Hydrolase family 7 (GH7). Known activities for members of family GH7 include endo-β-1,4-glucanase (EC 3.2.1.4); [reducing end-acting] cellobiohydrolase (EC 3.2.1.-); chitosanase (EC 3.2.1.132); endo-β-1,3-1,4-glucanase (EC 3.2.1.73)

Herein, a β-glucosidase (abbreviated BG) (EC 3.2.1.21) is any polypeptide which is capable of catalysing the hydrolysis of terminal, non-reducing β-D-glucose residues with release of β-D-glucose. Such a polypeptide may have a wide specificity for β-D-glucosides and may also hydrolyze one or more of the following: a β-D-galactoside, an α-L-arabinoside, a β-D-xyloside or a β-D-fucoside. This enzyme may also be referred to as amygdalase, β-D-glucoside glucohydrolase, cellobiase or gentiobiase.

Herein a β-(1,3)(1,4)-glucanase (EC 3.2.1.73) is any polypeptide which is capable of catalyzing the hydrolysis of 1,4-β-D-glucosidic linkages in β-D-glucans containing 1,3- and 1,4-bonds. Such a polypeptide may act on lichenin and cereal β-D-glucans, but not on β-D-glucans containing only 1,3- or 1,4-bonds. This enzyme may also be referred to as licheninase, 1,3-1,4-β-D-glucan 4-glucanohydrolase, β-glucanase, endo-β-1,3-1,4 glucanase, lichenase or mixed linkage β-glucanase. An alternative for this type of enzyme is EC 3.2.1.6, which is described as endo-1,3(4)-beta-glucanase. This type of enzyme hydrolyses 1,3- or 1,4-linkages in beta-D-glucans when the glucose residue whose reducing group is involved in the linkage to be hydrolysed is itself substituted at C-3. Alternative names include endo-1,3-beta-glucanase, laminarinase, 1,3-(1,3;1,4)-beta-D-glucan 3 (4) glucanohydrolase; substrates include laminarin, lichenin and cereal beta-D-glucans.

A composition according to the invention may comprise a GH61 family enzyme or any other enzyme having cellulase enhancing activity.

Cellulase enhancing activity is herein defined as enhancing the activity of at least one cellulase. When the beta-glucosidase protein of the invention is present in a mixture with one or more cellulase, for instance in a mixture with cellobiohydrolase (CBH) and beta-glucosidase (BG), it will enhance the activity of these cellulases, which will result in a higher activity of the mixture to degrade cellulose. The enzymes in the GH61 family were originally classified as a glycoside hydrolase family based on measurement of very weak endo-1,4-b-D-glucanase activity in one family member (endoglucanase (EC 3.2.1.4)). The structure and mode of action of these enzymes are certainly non-canonical and they cannot be considered as bona fide glycosidases. However, they are kept in the CAZy classification on the basis of their capacity to enhance the breakdown of lignocellulose when used in conjunction with a cellulase or a mixture of cellulases. An overview of known members of family GH61 is given in FIG. 5 of Harris, P V et al, Biochemistry 2010, 49, 3305-3316.

A composition of the invention may comprise any hemicellulase, for example, an endoxylanase, a β-xylosidase, a α-L-arabionofuranosidase, an α-D-glucuronidase, an acetyl xylan esterase, a feruloyl esterase, a coumaroyl esterase, an α-galactosidase, a β-galactosidase, a β-mannanase or a β-mannosidase.

Herein, an endoxylanase (EC 3.2.1.8) is any polypeptide which is capable of catalyzing the endohydrolysis of 1,4-β-D-xylosidic linkages in xylans. This enzyme may also be referred to as endo-1,4-β-xylanase or 1,4-β-D-xylan xylanohydrolase. An alternative is EC 3.2.1.136, a glucuronoarabinoxylan endoxylanase, an enzyme that is able to hydrolyse 1,4 xylosidic linkages in glucuronoarabinoxylans.

Herein, a β-xylosidase (EC 3.2.1.37) is any polypeptide which is capable of catalyzing the hydrolysis of 1,4-β-D-xylans, to remove successive D-xylose residues from the non-reducing termini. Such enzymes may also hydrolyze xylobiose. This enzyme may also be referred to as xylan 1,4-β-xylosidase, 1,4-β-D-xylan xylohydrolase, exo-1,4-β-xylosidase or xylobiase.

Herein, an α-L-arabinofuranosidase (EC 3.2.1.55) is any polypeptide which is capable of acting on α-L-arabinofuranosides, α-L-arabinans containing (1,2) and/or (1,3)- and/or (1,5)-linkages, arabinoxylans and arabinogalactans. This enzyme may also be referred to as α-N-arabinofuranosidase, arabinofuranosidase or arabinosidase.

Herein, an α-D-glucuronidase (EC 3.2.1.139) is any polypeptide which is capable of catalyzing a reaction of the following form: alpha-D-glucuronoside+H(2)O=an alcohol+D-glucuronate. This enzyme may also be referred to as alpha-glucuronidase or alpha-glucosiduronase. These enzymes may also hydrolyse 4-O-methylated glucoronic acid, which can also be present as a substituent in xylans. Alternative is EC 3.2.1.131: xylan alpha-1,2-glucuronosidase, which catalyses the hydrolysis of alpha-1,2-(4-O-methyl)glucuronosyl links.

Herein, an acetyl xylan esterase (EC 3.1.1.72) is any polypeptide which is capable of catalyzing the deacetylation of xylans and xylo-oligosaccharides. Such a polypeptide may catalyze the hydrolysis of acetyl groups from polymeric xylan, acetylated xylose, acetylated glucose, alpha-napthyl acetate or p-nitrophenyl acetate but, typically, not from triacylglycerol. Such a polypeptide typically does not act on acetylated mannan or pectin.

Herein, a feruloyl esterase (EC 3.1.1.73) is any polypeptide which is capable of catalyzing a reaction of the form: feruloyl-saccharide+H(2)O=ferulate+saccharide. The saccharide may be, for example, an oligosaccharide or a polysaccharide. It may typically catalyze the hydrolysis of the 4-hydroxy-3-methoxycinnamoyl(feruloyl) group from an esterified sugar, which is usually arabinose in 'natural' substrates. p-nitrophenol acetate and methyl ferulate are typically poorer substrates. This enzyme may also be referred to as cinnamoyl ester hydrolase, ferulic acid esterase or hydroxycinnamoyl esterase. It may also be referred to as a hemicellulase accessory enzyme, since it may help xylanases and pectinases to break down plant cell wall hemicellulose and pectin.

Herein, a coumaroyl esterase (EC 3.1.1.73) is any polypeptide which is capable of catalyzing a reaction of the form: coumaroyl-saccharide+H(2)O=coumarate+saccharide. The saccharide may be, for example, an oligosaccharide or a polysaccharide. This enzyme may also be referred to as trans-4-coumaroyl esterase, trans-p-coumaroyl esterase, p-coumaroyl esterase or p-coumaric acid esterase. This enzyme also falls within EC 3.1.1.73 so may also be referred to as a feruloyl esterase.

Herein, an α-galactosidase (EC 3.2.1.22) is any polypeptide which is capable of catalyzing the hydrolysis of terminal, non-reducing α-D-galactose residues in α-D-galactosides, including galactose oligosaccharides, galactomannans, galactans and arabinogalactans. Such a polypeptide may also be capable of hydrolyzing α-D-fucosides. This enzyme may also be referred to as melibiase.

Herein, a β-galactosidase (EC 3.2.1.23) is any polypeptide which is capable of catalyzing the hydrolysis of terminal non-reducing β-D-galactose residues in β-D-galactosides. Such a polypeptide may also be capable of hydrolyzing α-L-arabinosides. This enzyme may also be referred to as exo-(1->4)-β-D-galactanase or lactase.

Herein, a β-mannanase (EC 3.2.1.78) is any polypeptide which is capable of catalyzing the random hydrolysis of 1,4-β-D-mannosidic linkages in mannans, galactomannans and glucomannans. This enzyme may also be referred to as mannan endo-1,4-β-mannosidase or endo-1,4-mannanase.

Herein, a β-mannosidase (EC 3.2.1.25) is any polypeptide which is capable of catalyzing the hydrolysis of terminal, non-reducing β-D-mannose residues in β-D-mannosides. This enzyme may also be referred to as mannanase or mannase.

A composition of the invention may comprise any pectinase, for example an endo polygalacturonase, a pectin methyl esterase, an endo-galactanase, a beta galactosidase, a pectin acetyl esterase, an endo-pectin lyase, pectate lyase, alpha rhamnosidase, an exo-galacturonase, an exo-polygalacturonate lyase, a rhamnogalacturonan hydrolase, a rhamnogalacturonan lyase, a rhamnogalacturonan acetyl esterase, a rhamnogalacturonan galacturonohydrolase or a xylogalacturonase.

Herein, an endo-polygalacturonase (EC 3.2.1.15) is any polypeptide which is capable of catalyzing the random hydrolysis of 1,4-α-D-galactosiduronic linkages in pectate and other galacturonans. This enzyme may also be referred to as polygalacturonase pectin depolymerase, pectinase, endopolygalacturonase, pectolase, pectin hydrolase, pectin polygalacturonase, poly-α-1,4-galacturonide glycanohydrolase, endogalacturonase; endo-D-galacturonase or poly(1,4-α-D-galacturonide)glycanohydrolase.

Herein, a pectin methyl esterase (EC 3.1.1.11) is any enzyme which is capable of catalyzing the reaction: pectin+n H₂O=n methanol+pectate. The enzyme may also been known as pectinesterase, pectin demethoxylase, pectin methoxylase, pectin methylesterase, pectase, pectinoesterase or pectin pectylhydrolase.

Herein, an endo-galactanase (EC 3.2.1.89) is any enzyme capable of catalyzing the endohydrolysis of 1,4-β-D-galactosidic linkages in arabinogalactans. The enzyme may also be known as arabinogalactan endo-1,4-β-galactosidase, endo-1,4-β-galactanase, galactanase, arabinogalactanase or arabinogalactan 4-β-D-galactanohydrolase.

Herein, a pectin acetyl esterase is defined herein as any enzyme which has an acetyl esterase activity which catalyzes the deacetylation of the acetyl groups at the hydroxyl groups of GalUA residues of pectin Herein, an endo-pectin lyase (EC 4.2.2.10) is any enzyme capable of catalyzing the eliminative cleavage of (1→4)-α-D-galacturonan methyl ester to give oligosaccharides with 4-deoxy-6-O-methyl-α-D-galact-4-enuronosyl groups at their non-reducing ends. The enzyme may also be known as pectin lyase, pectin trans-eliminase; endo-pectin lyase, polymethylgalacturonic transeliminase, pectin methyltranseliminase, pectolyase, PL, PNL or PMGL or (1→4)-6-O-methyl-α-D-galacturonan lyase.

Herein, a pectate lyase (EC 4.2.2.2) is any enzyme capable of catalyzing the eliminative cleavage of (1→4)-α-D-galacturonan to give oligosaccharides with 4-deoxy-α-D-galact-4-enuronosyl groups at their non-reducing ends. The enzyme may also be known polygalacturonic transeliminase, pectic acid transeliminase, polygalacturonate lyase, endopectin methyltranseliminase, pectate transeliminase, endogalacturonate transeliminase, pectic acid lyase, pectic lyase, α-1,4-D-endopolygalacturonic acid lyase, PGA lyase, PPase-N, endo-α-1,4-polygalacturonic acid lyase, polygalacturonic acid lyase, pectin trans-eliminase, polygalacturonic acid trans-eliminase or (1→4)-α-D-galacturonan lyase.

Herein, an alpha rhamnosidase (EC 3.2.1.40) is any polypeptide which is capable of catalyzing the hydrolysis of terminal non-reducing α-L-rhamnose residues in α-L-rhamnosides or alternatively in rhamnogalacturonan. This enzyme may also be known as α-L-rhamnosidase T, α-L-rhamnosidase N or α-L-rhamnoside rhamnohydrolase.

Herein, exo-galacturonase (EC 3.2.1.82) is any polypeptide capable of hydrolysis of pectic acid from the non-reducing end, releasing digalacturonate. The enzyme may also be known as exo-poly-α-galacturonosidase, exopolygalacturonosidase or exopolygalacturanosidase.

Herein, exo-galacturonase (EC 3.2.1.67) is any polypeptide capable of catalyzing: $(1,4-\alpha-D-galacturonide)_n + H_2O =$ $(1,4-\alpha-D-galacturonide)_{n-1} + D-galacturonate$. The enzyme may also be known as galacturan 1,4-α-galacturonidase, exopolygalacturonase, poly(galacturonate) hydrolase, exo-D-galacturonase, exo-D-galacturonanase, exopoly-D-galacturonase or poly(1,4-α-D-galacturonide) galacturonohydrolase.

Herein, exopolygalacturonate lyase (EC 4.2.2.9) is any polypeptide capable of catalyzing eliminative cleavage of 4-(4-deoxy-α-D-galact-4-enuronosyl)-D-galacturonate from the reducing end of pectate, i.e. de-esterified pectin. This enzyme may be known as pectate disaccharide-lyase, pectate exo-lyase, exopectic acid transeliminase, exopectate lyase, exopolygalacturonic acid-trans-eliminase, PATE, exo-PATE, exo-PGL or (1→4)-α-D-galacturonan reducing-end-disaccharide-lyase.

Herein, rhamnogalacturonan hydrolase is any polypeptide which is capable of hydrolyzing the linkage between galactosyluronic acid and rhamnopyranosyl in an endo-fashion in strictly alternating rhamnogalacturonan structures, consisting of the disaccharide [(1,2-alpha-L-rhamnoyl-(1,4)-alpha-galactosyluronic acid].

Herein, rhamnogalacturonan lyase is any polypeptide which is any polypeptide which is capable of cleaving α-L-Rhap-(1→4)-α-D-GalpA linkages in an endo-fashion in rhamnogalacturonan by beta-elimination.

Herein, rhamnogalacturonan acetyl esterase is any polypeptide which catalyzes the deacetylation of the backbone of alternating rhamnose and galacturonic acid residues in rhamnogalacturonan.

Herein, rhamnogalacturonan galacturonohydrolase is any polypeptide which is capable of hydrolyzing galacturonic acid from the non-reducing end of strictly alternating rhamnogalacturonan structures in an exo-fashion.

Herein, xylogalacturonase is any polypeptide which acts on xylogalacturonan by cleaving the β-xylose substituted galacturonic acid backbone in an endo-manner. This enzyme may also be known as xylogalacturonan hydrolase.

Herein, an α-L-arabinofuranosidase (EC 3.2.1.55) is any polypeptide which is capable of acting on α-L-arabinofuranosides, α-L-arabinans containing (1,2) and/or (1,3)- and/or (1,5)-linkages, arabinoxylans and arabinogalactans. This enzyme may also be referred to as α-N-arabinofuranosidase, arabinofuranosidase or arabinosidase.

Herein, endo-arabinanase (EC 3.2.1.99) is any polypeptide which is capable of catalyzing endohydrolysis of 1,5-α-arabinofuranosidic linkages in 1,5-arabinans. The enzyme may also be know as endo-arabinase, arabinan endo-1,5-α-L-arabinosidase, endo-1,5-α-L-arabinanase, endo-α-1,5-arabanase; endo-arabanase or 1,5-α-L-arabinan 1,5-α-L-arabinanohydrolase.

A composition of the invention will typically comprise at least one cellulase and/or at least one hemicellulase and/or at least one pectinase (one of which is a polypeptide according to the invention). A composition of the invention may comprise a cellobiohydrolase, an endoglucanase and/or a β-glucosidase. Such a composition may also comprise one or more hemicellulases and/or one or more pectinases.

One or more (for example two, three, four or all) of an amylase, a protease, a lipase, a ligninase, a hexosyltransferase or a glucuronidase may be present in a composition of the invention.

"Protease" includes enzymes that hydrolyze peptide bonds (peptidases), as well as enzymes that hydrolyze bonds between peptides and other moieties, such as sugars (glycopeptidases). Many proteases are characterized under EC 3.4, and are suitable for use in the invention incorporated herein by reference. Some specific types of proteases include, cysteine proteases including pepsin, papain and serine proteases including chymotrypsins, carboxypeptidases and metalloendopeptidases.

"Lipase" includes enzymes that hydrolyze lipids, fatty acids, and acylglycerides, including phospoglycerides, lipoproteins, diacylglycerols, and the like. In plants, lipids are used as structural components to limit water loss and pathogen infection. These lipids include waxes derived from fatty acids, as well as cutin and suberin.

"Ligninase" includes enzymes that can hydrolyze or break down the structure of lignin polymers. Enzymes that can break down lignin include lignin peroxidases, manganese peroxidases, laccases and feruloyl esterases, and other enzymes described in the art known to depolymerize or otherwise break lignin polymers. Also included are enzymes capable of hydrolyzing bonds formed between hemicellulosic sugars (notably arabinose) and lignin. Ligninases include but are not limited to the following group of enzymes: lignin peroxidases (EC 1.11.14), manganese peroxidases (EC 1.11.1.13), laccases (EC 1.10.3.2) and feruloyl esterases (EC 3.1.1.73).

"Hexosyltransferase" (2.4.1-) includes enzymes which are capable of transferring glycosyl groups, more specifically hexosyl groups. In addition to transfer of a glycosyl-group from a glycosyl-containing donor to another glycosyl-containing compound, the acceptor, the enzymes can also transfer the glycosyl-group to water as an acceptor. This reaction is also known as a hydrolysis reaction, instead of a transfer reaction. An example of a hexosyltransferase which may be used in the invention is a β-glucanosyltransferase. Such an enzyme may be able to catalyze degradation of (1,3)(1,4) glucan and/or cellulose and/or a cellulose degradation product.

"Glucuronidase" includes enzymes that catalyze the hydrolysis of a glucoronoside, for example β-glucuronoside to yield an alcohol. Many glucuronidases have been characterized and may be suitable for use in the invention, for example β-glucuronidase (EC 3.2.1.31), hyaluronidase-glucuronidase (EC 3.2.1.36), glucuronosyl-disulfoglucosamine glucuronidase (3.2.1.56), glycyrrhizinate β-glucuronidase (3.2.1.128) or α-D-glucuronidase (EC 3.2.1.139).

A composition of the invention may comprise an expansin or expansin-like protein, such as a swollenin (see Salheimo et al., Eur. J. Biohem. 269, 4202-4211, 2002) or a swollenin-like protein.

Expansins are implicated in loosening of the cell wall structure during plant cell growth. Expansins have been proposed to disrupt hydrogen bonding between cellulose and other cell wall polysaccharides without having hydrolytic activity. In this way, they are thought to allow the sliding of cellulose fibers and enlargement of the cell wall. Swollenin, an expansin-like protein contains an N-terminal Carbohydrate Binding Module Family 1 domain (CBD) and a C-terminal expansin-like domain. For the purposes of this invention, an expansin-like protein or swollenin-like protein may comprise one or both of such domains and/or may disrupt the structure of cell walls (such as disrupting cellulose structure), optionally without producing detectable amounts of reducing sugars.

A composition of the invention may comprise the polypeptide product of a cellulose integrating protein, scaffoldin or a scaffoldin-like protein, for example CipA or CipC from *Clostridium thermocellum* or *Clostridium cellulolyticum* respectively.

Scaffoldins and cellulose integrating proteins are multifunctional integrating subunits which may organize cellulolytic subunits into a multi-enzyme complex. This is accomplished by the interaction of two complementary classes of domain, i.e. a cohesion domain on scaffoldin and a dockerin domain on each enzymatic unit. The scaffoldin subunit also bears a cellulose-binding module (CBM) that mediates attachment of the cellulosome to its substrate. A scaffoldin or cellulose integrating protein for the purposes of this invention may comprise one or both of such domains.

A composition of the invention may comprise a cellulose induced protein or modulating protein, for example as encoded by cip1 or cip2 gene or similar genes from *Trichoderma reesei/Hypocrea jecorina* (see Foreman et al., J. Biol. Chem. 278(34), 31988-31997, 2003). The polypeptide product of these genes are bimodular proteins, which contain a cellulose binding module and a domain which function or activity can not be related to known glycosyl hydrolase families. Yet, the presence of a cellulose binding module and the coregulation of the expression of these genes with cellulases components indicates previously unrecognised activities with potential role in biomass degradation.

A composition of the invention may be composed of a member of each of the classes of the polypeptides mentioned above, several members of one polypeptide class, or any combination of these polypeptide classes.

A composition of the invention may be composed of polypeptides, for example enzymes, from (1) commercial suppliers; (2) cloned genes expressing polypeptides, for example enzymes; (3) complex broth (such as that resulting from growth of a microbial strain in media, wherein the strains secrete proteins and enzymes into the media; (4) cell lysates of strains grown as in (3); and/or (5) plant material expressing polypeptides, for example enzymes. Different polypeptides, for example enzymes in a composition of the invention may be obtained from different sources.

Use of the Polypeptides

The polypeptides and polypeptide compositions according to the invention may be used in many different applications. For instance they may be used to produce fermentable sugars. The fermentable sugars can then, as part of a biofuel process, be converted into biogas or ethanol, butanol, isobutanol, 2 butanol or other suitable substances. Alternatively the polypeptides and their compositions may be used as enzyme, for instance in production of food products, in detergent compositions, in the paper and pulp industry and in antibacterial formulations, in pharmaceutical products such as throat lozenges, toothpastes, and mouthwash. Some of the uses will be illustrated in more detail below.

In the uses and methods described below, the components of the compositions described above may be provided concomitantly (i.e. as a single composition per se) or separately or sequentially.

The invention also relates to the use of the beta-glucosidase polypeptide according to the invention and compositions comprising such an enzyme in industrial processes.

Despite the long term experience obtained with these processes, the beta-glucosidase polypeptide according to the invention may feature a number of significant advantages over enzymes currently used. Depending on the specific application, these advantages may include aspects such as lower production costs, higher specificity towards the substrate, reduced antigenicity, fewer undesirable side activities, higher yields when produced in a suitable microorganism, more suitable pH and temperature ranges, non-inhibition by hydrophobic, lignin-derived products or less product inhibition or, in the case of the food industry a better taste or texture of a final product as well as food grade and kosher aspects.

In principle, a beta-glucosidase polypeptide or composition of the invention may be used in any process which requires the treatment of a material which comprises polysaccharide. Thus, a polypeptide or composition of the invention may be used in the treatment of polysaccharide material. Herein, polysaccharide material is a material which comprises or consists essential of one or, more typically, more than one polysaccharide.

Typically, plants and material derived therefrom comprise significant quantities of non-starch polysaccharide material. Accordingly, a polypeptide of the invention may be used in the treatment of a plant or fungal material or a material derived therefrom.

Lignocellulose

An important component of plant non-starch polysaccharide material is lignocellulose (also referred to herein as lignocellulolytic biomass). Lignocellulose is plant material that comprises cellulose and hemicellulose and lignin. The carbohydrate polymers (cellulose and hemicelluloses) are tightly bound to the lignin by hydrogen and covalent bonds. Accordingly, a polypeptide of the invention may be used in the treatment of lignocellulolytic material. Herein, lignocellulolytic material is a material which comprises or consists essential of lignocellulose. Thus, in a method of the invention for the treatment of a non-starch polysaccharide, the non-starch polysaccharide may be a lignocellulosic material/biomass.

Accordingly, the invention provides a method of treating a substrate comprising non-starch polysaccharide in which the treatment comprises the degradation and/or hydrolysis and/or modification of cellulose and/or hemicellulose and/or a pectic substance.

Degradation in this context indicates that the treatment results in the generation of hydrolysis products of cellulose and/or hemicellulose and/or a pectic substance, i.e. saccharides of shorter length are present as result of the treatment than are present in a similar untreated non-starch polysaccharide. Thus, degradation in this context may result in the liberation of oligosaccharides and/or sugar monomers.

All plants contain non-starch polysaccharide as do virtually all plant-derived polysaccharide materials. Accordingly, in a method of the invention for the treatment of substrate comprising a non-starch polysaccharide, said substrate may be provided in the form of a plant or a plant derived material or a material comprising a plant or plant derived material, for example a plant pulp, a plant extract, a foodstuff or ingredient therefore, a fabric, a textile or an item of clothing.

Lignocellulolytic biomass suitable for use in the invention includes biomass and can include virgin biomass and/or non-virgin biomass such as agricultural biomass, commercial organics, construction and demolition debris, municipal solid waste, waste paper and yard waste. Common forms of biomass include trees, shrubs and grasses, wheat, wheat straw, sugar cane bagasse, corn, corn husks, corn cobs, corn kernel including fiber from kernels, products and by-products from milling of grains such as corn, wheat and barley (including wet milling and dry milling) often called "bran or fibre" as well as municipal solid waste, waste paper and yard waste. The biomass can also be, but is not limited to, herbaceous material, agricultural residues, forestry residues, municipal solid wastes, waste paper, and pulp and paper mill residues. "Agricultural biomass" includes branches, bushes, canes, corn and corn husks, energy crops, forests, fruits, flowers, grains, grasses, herbaceous crops, leaves, bark, needles, logs, roots, saplings, short rotation woody crops, shrubs, switch grasses, trees, vegetables, fruit peels, vines, sugar beet pulp, wheat midlings, oat hulls, and hard and soft woods (not including woods with deleterious materials). In addition, agricultural biomass includes organic waste materials generated from agricultural processes including farming and forestry activities, specifically including forestry wood waste. Agricultural biomass may be any of the aforestated singularly or in any combination or mixture thereof. Further examples of suitable biomass are orchard primings, chaparral, mill waste, urban wood waste, municipal waste, logging waste, forest thinnings, short-rotation woody crops, industrial waste, wheat straw, oat straw, rice straw, barley straw, rye straw, flax straw, soy hulls, rice hulls, rice straw, corn gluten feed, oat hulls, sugar cane, corn stover, corn stalks, corn cobs, corn husks, prairie grass, gamagrass, foxtail; sugar beet pulp, citrus fruit pulp, seed hulls, cellulosic animal wastes, lawn clippings, cotton, seaweed, trees, shrubs, grasses, wheat, wheat straw, sugar cane bagasse, corn, corn husks, corn hobs, corn kernel, fiber from kernels, products and by-products from wet or dry milling of grains, municipal solid waste, waste paper, yard waste, herbaceous material, agricultural residues, forestry residues, municipal solid waste, waste paper, pulp, paper mill residues, branches, bushes, canes, corn, corn husks, an energy crop, forest, a fruit, a flower, a grain, a grass, a herbaceous crop, a leaf, bark, a needle, a log, a root, a sapling, a shrub, switch grass, a tree, a vegetable, fruit peel, a vine, sugar beet pulp, wheat midlings, oat hulls, hard or soft wood, organic waste material generated from an agricultural process, forestry wood waste, or a combination of any two or more thereof.

Apart from virgin biomass or feedstocks already processed in food and feed or paper and pulping industries, the biomass/feedstock may additionally be pretreated with heat, mechanical and/or chemical modification or any combination of such methods in order to enhance enzymatic degradation.

Pretreatment

Before enzymatic treatment, the feedstock may optionally be pre-treated with heat, mechanical and/or chemical modification or any combination of such methods in order to enhance the accessibility of the substrate to enzymatic hydrolysis and/or hydrolyse the hemicellulose and/or solubilize the hemicellulose and/or cellulose and/or lignin, in any way known in the art. The pretreatment may comprise exposing the lignocellulosic material to (hot) water, steam (steam explosion), an acid, a base, a solvent, heat, a peroxide, ozone, mechanical shredding, grinding, milling or rapid depressurization, or a combination of any two or more thereof. A chemical pretreatment is often combined with heat-pretreatment, e.g. between 150-220° C. for 1 to 30 minutes.

Presaccharifation

After the pretreatment step, a liquefaction/hydrolysis or presaccharification step involving incubation with an enzyme or enzyme mixture can be utilized. The presaccharification step can be performed at many different temperatures but it is preferred that the presaccharification step occur at the temperature best suited to the enzyme mix being applied, or the predicted enzyme optimum of the enzymes to be applied. The temperature of the presaccharification step may range from about 10° C. to about 95° C., about 20° C. to about 85° C., about 30° C. to about 70° C., about 40° C. to about 60° C., about 37° C. to about 50° C., preferably about 37° C. to about 80° C., more preferably about 60-70° C. even more preferably around 65° C. The pH of the presaccharification mixture may range from about 2.0 to about 10.0, but is preferably about 3.0 to about 7.0, more preferably about 4.0 to about 6.0, even more preferably about 4.0 to about 5.0. Again, the pH may be adjusted to maximize enzyme activity and may be adjusted with the addition of the enzyme.

The liquefaction/hydrolysis or presaccharification step reaction may occur from several minutes to several hours, such as from about 1 hour to about 120 hours, preferably from about 2 hours to about 48 hours, more preferably from about 2 to about 24 hours, most preferably for from about 2 to about 6 hours. The cellulase treatment may occur from several minutes to several hours, such as from about 6 hours to about 120 hours, preferably about 12 hours to about 72 hours, more preferably about 24 to 48 hours.

Saccharification

The invention provides a method for producing a sugar from a lignocellulosic material which method comprises contacting a polypeptide of the invention to a composition of the invention with the lignocellulosic material.

Such a method allows free sugars (monomers) and/or oligosaccharides to be generated from lignocellulosic biomass. These methods involve converting lignocellulosic biomass to free sugars and small oligosaccharides with a polypeptide or composition of the invention.

The process of converting a complex carbohydrate such as lignocellulose into sugars preferably allows conversion into fermentable sugars. Such a process may be referred to as "saccharification." Accordingly, a method of the invention may result in the liberation of one or more hexose and/or pentose sugars, such as one or more of glucose, xylose, arabinose, galactose, galacturonic acid, glucuronic acid, mannose, rhamnose, ribose and fructose.

Accordingly, another aspect of the invention includes methods that utilize the polypeptide of composition of the invention described above together with further enzymes or physical treatments such as temperature and pH to convert the lignocellulosic plant biomass to sugars and oligosaccharides.

While the composition has been discussed as a single mixture it is recognized that the enzymes may be added sequentially where the temperature, pH, and other conditions may be altered to increase the activity of each individual enzyme. Alternatively, an optimum pH and temperature can be determined for the enzyme mixture.

The enzymes are reacted with substrate under any appropriate conditions. For example, enzymes can be incubated at about 25° C., about 30° C., about 35° C., about 37° C., about 40° C., about 45° C., about 50° C., about 55° C., about 60° C., about 65° C., about 70° C., about 75° C., about 80° C., about 85° C., about 90° C. or higher. That is, they can be incubated at a temperature of from about 20° C. to about 95° C., for example in buffers of low to medium ionic strength and/or from low to neutral pH. By "medium ionic strength" is intended that the buffer has an ion concentration of about 200 millimolar (mM) or less for any single ion component. The pH may range from about pH 2.5, about pH 3.0, about pH 3.5, about pH 4.0, about pH 4.5, about pH 5, about pH 5.5, about pH 6, about pH 6.5, about pH 7, about pH 7.5, about pH 8.0, to about pH 8.5. Generally, the pH range will be from about pH 3.0 to about pH 7. For the production of ethanol an acidic medium is preferred, e.g. pH=4, whereas for the production of biogas neutral pH, e.g. pH=7 is desirable. Incubation of enzyme combinations under these conditions results in release or liberation of substantial amounts of the sugar from the lignocellulose. By substantial amount is intended at least 20%, 30%, 40%, 50%, 60%, 70%, 80%, 90%, 95% or more of available sugar.

The polypeptides, such as enzymes, can be produced either exogenously in microorganisms, yeasts, fungi, bacteria or plants, then isolated and added, for example, to lignocellulosic feedstock. Alternatively, the enzymes are produced, but not isolated, and crude cell mass fermentation broth, or plant material (such as corn stover), and the like may be added to, for example, the feedstock. Alternatively, the crude cell mass or enzyme production medium or plant material may be treated to prevent further microbial growth (for example, by heating or addition of antimicrobial agents), then added to, for example, a feedstock. These crude enzyme mixtures may include the organism producing the enzyme. Alternatively, the enzyme may be produced in a fermentation that uses feedstock (such as corn stover) to provide nutrition to an organism that produces an enzyme(s). In this manner, plants that produce the enzymes may themselves serve as a lignocellulosic feedstock and be added into lignocellulosic feedstock.

Fermentation of Sugars

The fermentable sugars can be converted to useful value-added fermentation products, non-limiting examples of which include amino acids, vitamins, pharmaceuticals, animal feed supplements, specialty chemicals, chemical feedstocks, plastics, solvents, fuels, or other organic polymers, lactic acid, and ethanol, including fuel ethanol. In particular the sugars may be used as feedstocks for fermentation into chemicals, plastics, such as for instance succinic acid and (bio) fuels, including ethanol, methanol, butanol synthetic liquid fuels and biogas.

For instance, in the method of the invention, an enzyme or combination of enzymes acts on a lignocellulosic substrate or plant biomass, serving as the feedstock, so as to convert this complex substrate to simple sugars and oligosaccharides for the production of ethanol or other useful fermentation products.

Sugars released from biomass can be converted to useful fermentation products such a one of those including, but not limited to, amino acids, vitamins, pharmaceuticals, animal feed supplements, specialty chemicals, chemical feedstocks, plastics, and ethanol, including fuel ethanol.

Accordingly, the invention provides a method for the preparation of a fermentation product, which method comprises:
 a. degrading lignocellulose using a method as described herein; and
 b. fermentation of the resulting material,
thereby to prepare a fermentation product.

The fermentation may be carried out under aerobic or anaerobic conditions. Preferably, the process is carried out under micro-aerophilic or oxygen limited conditions.

An anaerobic fermentation process is herein defined as a fermentation process run in the absence of oxygen or in which substantially no oxygen is consumed, preferably about 5 or less, about 2.5 or less or about 1 mmol/L/h or less, and wherein organic molecules serve as both electron donor and electron acceptors.

An oxygen-limited fermentation process is a process in which the oxygen consumption is limited by the oxygen transfer from the gas to the liquid. The degree of oxygen limitation is determined by the amount and composition of the ingoing gasflow as well as the actual mixing/mass transfer properties of the fermentation equipment used. Preferably, in a process under oxygen-limited conditions, the rate of oxygen consumption is at least about 5.5, more preferably at least about 6 and even more preferably at least about 7 mmol/L/h.

A method for the preparation of a fermentation product may optionally comprise recovery of the fermentation product.

SSF

Fermentation and Saccharification may also be executed in Simultaneous Saccharification and Fermentation (SSF) mode. One of the advantages of this mode is reduction of the sugar inhibition on enzymatic hydrolysis (Sugar inhibition on cellulases is described by Caminal B&B Vol XXVII Pp 1282-1290).

Fermentation Products

Fermentation products which may be produced according to the invention include amino acids, vitamins, pharmaceuticals, animal feed supplements, specialty chemicals, chemical feedstocks, plastics, solvents, fuels, or other organic polymers, lactic acid, and ethanol, including fuel ethanol (the term "ethanol" being understood to include ethyl alcohol or mixtures of ethyl alcohol and water).

Specific value-added products that may be produced by the methods of the invention include, but not limited to, biofuels (including ethanol and butanol and a biogas); lactic acid; a plastic; a specialty chemical; an organic acid, including citric acid, succinic acid, fumaric acid, itaconic acid and maleic acid; 3-hydoxy-propionic acid, acrylic acid; acetic acid; 1,3-propane-diol; ethylene, glycerol; a solvent; an animal feed supplement; a pharmaceutical, such as a β-lactam antibiotic or a cephalosporin; vitamins; an amino acid, such as lysine, methionine, tryptophan, threonine, and aspartic acid; an industrial enzyme, such as a protease, a cellulase, an amylase, a glucanase, a lactase, a lipase, a lyase, an oxidoreductases, a transferase or a xylanase; and a chemical feedstock.

Biogas

The invention also provides use of a polypeptide or composition a described herein in a method for the preparation of biogas. Biogas typically refers to a gas produced by the biological breakdown of organic matter, for example non-starch carbohydrate containing material, in the absence of oxygen. Biogas originates from biogenic material and is a type of biofuel. One type of biogas is produced by anaerobic digestion or fermentation of biodegradable materials such as biomass, manure or sewage, municipal waste, and energy crops. This type of biogas is comprised primarily of methane and carbon dioxide. The gas methane can be combusted or oxidized with oxygen. Air contains 21% oxygen. This energy release allows biogas to be used as a fuel. Biogas can be used as a low-cost fuel in any country for any heating purpose, such as cooking. It can also be utilized in modern waste management facilities where it can be used to run any type of heat engine, to generate either mechanical or electrical power.

The first step in microbial biogas production consists in the enzymatic degradation of polymers and complex substrates (for example non-starch carbohydrate). Accordingly, the invention provides a method for preparation of a biogas in which a substrate comprising non-starch carbohydrate is contacted with a polypeptide or composition of the invention, thereby to yield fermentable material which may be converted into a biogas by an organism such as a microorganism. In such a method, a polypeptide of the invention may be provided by way of an organism, for example a microorganism which expresses such a polypeptide.

Use of Enzymes in Food Products

The polypeptides and compositions of the invention may be used in a method of processing plant material to degrade or modify the cellulose or hemicellulose or pectic substance constituents of the cell walls of the plant or fungal material. Such methods may be useful in the preparation of food product. Accordingly, the invention provides a method for preparing a food product which method comprises incorporating a polypeptide or composition of the invention during preparation of the food product.

The invention also provides a method of processing a plant material which method comprises contacting the plant material with a polypeptide or composition of the invention to degrade or modify the cellulose in the (plant) material. Preferably, the plant material is a plant pulp or plant extract, such as juices.

Plant and cellulose/hemicellulose/pectic substance-containing materials include plant pulp, parts of plants and plant extracts. In the context of this invention an extract from a plant material is any substance which can be derived from plant material by extraction (mechanical and/or chemical), processing or by other separation techniques. The extract may be juice, nectar, base, or concentrates made thereof. The plant material may comprise or be derived from vegetables, e.g., carrots, celery, onions, legumes or leguminous plants (soy, soybean, peas) or fruit, e.g., pome or seed fruit (apples, pears, quince etc.), grapes, tomatoes, citrus (orange, lemon, lime, mandarin), melons, prunes, cherries, black currants, redcurrants, raspberries, strawberries, cranberries, pineapple and other tropical fruits, trees and parts thereof (e.g. pollen, from pine trees), or cereal (oats, barley, wheat, maize, rice). The material (to be hydrolysed) may also be agricultural residues, such as sugar beet pulp, corn cobs, wheat straw, (ground) nutshells, or recyclable materials, e.g. (waste) paper.

The polypeptides of the invention can thus be used to treat plant material including plant pulp and plant extracts. They may also be used to treat liquid or solid foodstuffs or edible foodstuff ingredients, or be used in the extraction of plant oils, starch or as a thickener in foods.

Typically, the polypeptides of the invention are used as a composition/enzyme preparation as described above. The composition will generally be added to plant pulp obtainable by, for example mechanical processing such as crushing or milling plant material. Incubation of the composition with the plant will typically be carried out for at time of from 10 minutes to 5 hours, such as 30 minutes to 2 hours, preferably for about 1 hour. The processing temperature is preferably from about 10° C. to about 55° C., e.g. from about 15° C. to about 25° C., optimally about 20° C. and one can use from about 10 g to about 300 g, preferably from about 30 g to about 70 g, optimally about 50 g of enzyme per ton of material to be treated.

All of the enzyme(s) or their compositions used may be added sequentially or at the same time to the plant pulp. Depending on the composition of the enzyme preparation the plant material may first be macerated (e.g. to a pure) or liquefied. Using the polypeptides of the invention processing parameters such as the yield of the extraction, viscosity of the extract and/or quality of the extract can be improved.

Alternatively, or in addition to the above, a polypeptide of the invention may be added to the raw juice obtained from pressing or liquefying the plant pulp. Treatment of the raw juice will be carried out in a similar manner to the plant pulp in respect of dosage, temperature and holding time. Again, other enzymes such as those discussed previously may be included. Typical incubation conditions are as described in the previous paragraph.

Once the raw juice has been incubated with the polypeptides of the invention, the juice is then centrifuged or (ultra) filtered to produce the final product.

After treatment with the polypeptide of the invention the (end) product can be heat treated, e.g. at about 100° C. for a time of from about 1 minute to about 1 hour, under conditions to partially or fully inactivate the polypeptide(s) of the invention.

A composition containing a polypeptide of the invention may also be used during the preparation of fruit or vegetable purees.

In baking the polypeptide may improve the dough structure, modify its stickiness or suppleness, improve the loaf volume and/or crumb structure or impart better textural characteristics such as break, shread or crumb quality.

The present invention thus relates to methods for preparing a dough or a cereal-based food product comprising incorporating into the dough a polypeptide or composition of the present invention. This may improve one or more properties of the dough or the cereal-based food product obtained from the dough relative to a dough or a cereal-based food product in which the polypeptide is not incorporated.

The preparation of the cereal-based food product according to the invention further can comprise steps known in the art such as boiling, drying, frying, steaming or baking of the obtained dough.

Products that are made from a dough that is boiled are for example boiled noodles, dumplings, products that are made from fried dough are for example doughnuts, beignets, fried noodles, products that are made for steamed dough are for example steamed buns and steamed noodles, examples of products made from dried dough are pasta and dried noodles and examples of products made from baked dough are bread, cookies, cake.

The term "improved property" is defined herein as any property of a dough and/or a product obtained from the dough, particularly a cereal-based food product, which is improved by the action of the polypeptide according to the invention relative to a dough or product in which the polypeptide according to the invention is not incorporated. The improved property may include, but is not limited to, increased strength of the dough, increased elasticity of the dough, increased stability of the dough, improved machineability of the dough, improved proofing resistance of the dough, reduced stickiness of the dough, improved extensibility of the dough, increased volume of the cereal-based food product, reduced blistering of the cereal-based food product, improved crumb structure of the baked product, improved softness of the cereal-based food product, improved flavour of the cereal-based food product, improved anti-staling of the cereal-based food product. Improved properties related to pasta and noodle type of cereal-based products are for example improved firmness, reduced stickiness, improved cohesiveness and reduced cooking loss.

The improved property may be determined by comparison of a dough and/or a cereal-based food product prepared with and without addition of a polypeptide of the present invention. Organoleptic qualities may be evaluated using procedures well established in the baking industry, and may include, for example, the use of a panel of trained taste-testers.

The term "dough" is defined herein as a mixture of cereal flour and other ingredients firm enough to knead or roll. Examples of cereals are wheat, rye, corn, maize, barley, rice, groats, buckwheat and oat. Wheat is I here and hereafter intended to encompass all known species of *Triticum* genus, for example *aestivum, durum* and/or *spelta*. Examples of suitable other ingredients are: the beta-glucosidase polypeptide according to the present invention, additional enzymes, chemical additives and/or processing aids. The dough may be fresh, frozen, pre-pared, or pre-baked. The preparation of a dough from the ingredients described above is well known in the art and comprises mixing of said ingredients and processing aids and one or more moulding and optionally fermentation steps. The preparation of frozen dough is described by Kulp and Lorenz in Frozen and Refrigerated Doughs and Batters.

The term "cereal-based food product" is defined herein as any product prepared from a dough, either of a soft or a crisp character. Examples of cereal-based food products, whether of a white, light or dark type, which may be advantageously produced by the present invention are bread (in particular white, whole-meal or rye bread), typically in the form of loaves or rolls, French baguette-type bread, pasta, noodles, doughnuts, bagels, cake, pita bread, tortillas, tacos, cakes, pancakes, biscuits, cookies, pie crusts, steamed bread, and crisp bread, and the like.

The term "baked product" is defined herein as any cereal-based food product prepared by baking the dough.

Non-starch polysaccharides (NSP) can increase the viscosity of the digesta which can, in turn, decrease nutrient availability and animal performance. The use of the beta-glucosidase polypeptide of the present invention can improve phosphorus utilization as well as cation minerals and polypeptide during animal digesta.

Adding specific nutrients to feed improves animal digestion and thereby reduces feed costs. A lot of feed additives are being currently used and new concepts are continuously developed. Use of specific enzymes like non-starch carbohydrate degrading enzymes could breakdown the fibre releasing energy as well as increasing the protein digestibility due to better accessibility of the protein when the fibre gets broken down. In this way the feed cost could come down as well as the protein levels in the feed also could be reduced.

Non-starch polysaccharides (NSPs) are also present in virtually all feed ingredients of plant origin. NSPs are poorly utilized and can, when solubilized, exert adverse effects on digestion. Exogenous enzymes can contribute to a better utilization of these NSPs and as a consequence reduce any anti-nutritional effects. Non-starch carbohydrate degrading enzymes of the present invention can be used for this purpose in cereal-based diets for poultry and, to a lesser extent, for pigs and other species.

A non-starch carbohydrate degrading polypeptide/enzyme of the invention (of a composition comprising the polypeptide/enzyme of the invention) may be used in the detergent industry, for example for removal from laundry of carbohydrate-based stains. A detergent composition may comprise a polypeptide/enzyme of the invention and, in addition, one or more of a cellulose, a hemicellulase, a pectinase, a protease, a lipase, a cutinase, an amylase or a carbohydrase.

Use of Enzymes in Detergent Compositions

A detergent composition comprising a polypeptide or composition of the invention may be in any convenient form, for example a paste, a gel, a powder or a liquid. A liquid detergent may be aqueous, typically containing up to about 70% water and from about 0 to about 30% organic solvent or non-aqueous material.

Such a detergent composition may, for example, be formulated as a hand or machine laundry detergent composition including a laundry additive composition suitable for pre-treatment of stained fabrics and a rinse added fabric softener composition, or be formulated as a detergent composition for use in general household hard surface cleaning operations, or be formulated for hand or machine dish washing operations.

In general, the properties of the enzyme should be compatible with the aselected detergent (for example, pH-optimum, compatibility with other enzymatic and/or non-enzymatic ingredients, etc.) and the enzyme(s) should be present in an effective amount.

A detergent composition may comprise a surfactant, for example an anionic or non-ionic surfactant, a detergent builder or complexing agent, one or more polymers, a bleaching system (for example an $H_2O_2$ source) or an enzyme stabilizer. A detergent composition may also comprise any other conventional detergent ingredient such as, for example, a conditioner including a clay, a foam booster, a sud suppressor, an anti-corrosion agent, a soil-suspending agent, an an-soil redeposition agent, a dye, a bactericide, an optical brightener, a hydrotropes, a tarnish inhibitor or a perfume.

Use of Enzymes in Paper and Pulp Processing

A polypeptide or composition of the present invention may be used in the paper and pulp industry, inter alia in the bleaching process to enhance the brightness of bleached pulps whereby the amount of chlorine used in the bleaching stages may be reduced, and to increase the freeness of pulps in the recycled paper process (Eriksson, K. E. L., Wood Science and Technology 24 (1990):79-101; Paice, et al., Biotechnol. and Bioeng. 32 (1988):235-239 and Pommier et al., Tappi Journal (1989):187-191). Furthermore, a polypeptide or composition of the invention may be used for treatment of lignocellulosic pulp so as to improve the bleachability thereof. Thereby the amount of chlorine need to obtain a satisfactory bleaching of the pulp may be reduced.

A polypeptide or composition of the invention may be used in a method of reducing the rate at which cellulose-containing fabrics become harsh or of reducing the harshness of cellulose-containing fabrics, the method comprising treating cellulose-containing fabrics with a polypeptide or composition as described above. The present invention further relates to a method providing colour clarification of coloured cellulose-containing fabrics, the method comprising treating coloured cellulose-containing fabrics with a polypeptide or composition as described above, and a method of providing a localized variation in colour of coloured cellulose-containing fabrics, the method comprising treating coloured cellulose-containing fabrics with a polypeptide or composition as described above. The methods of the invention may be carried out by treating cellulose-containing fabrics during washing. However, if desired, treatment of the fabrics may also be carried out during soaking or rinsing or simply by adding the polypeptide or composition as described above to water in which the fabrics are or will be immersed.

Other Enzyme Uses

In addition, a polypeptide or composition of the present invention can also be used in antibacterial formulation as well as in pharmaceutical products such as throat lozenges, toothpastes, and mouthwash.

The following Examples illustrate the invention:

EXAMPLES

Materials and Methods

DNA Procedures

Standard DNA procedures were carried out as described elsewhere (Sambrook et al., 1989, Molecular cloning: a laboratory manual, $2^{nd}$ Ed., Cold Spring Harbor Laboratory Press, Cold Spring Harbor, N.Y.) unless otherwise stated. DNA was amplified using the proofreading enzyme Physion polymerase (Finnzymes). Restriction enzymes were from Invitrogen or New England Biolabs.

Preparation of Cellulase Samples

Cellulases originating from *Talaromyces emersonii* were expressed in *Aspergillus niger*. Concentrated filtrates of the enzymes were produced as described in WO2004/030468. After growing *Aspergillus niger* containing the proper expression plasmids cell free supernatants were prepared by centrifugation of the fermentation broth at 5000×g for 30 minutes at 4° C. Optional the supernatant can be adjusted to pH=5 with 4 N KOH and sterile filtrated over a 2 μm (bottle-top) filter with suction to remove any fungal material. In addition the supernatants can be filtered further over a GF/A Whatmann Glass microfiber filter (150 mm Ø) to remove any solids. The supernatants were ultrafiltrated, concentrated, and stored until use at 4° C. or frozen at −20° C.

Method for Total Protein Determination

The method was a combination of precipitation of protein using trichloro acetic acid (TCA) to remove disturbing substances and allow determination of the protein concentration with the colorimetric Biuret reaction. In the Biuret reaction, a copper (II) ion is reduced to copper (I), which forms a complex with the nitrogens and carbons of the peptide bonds in an alkaline solution. A violet color indicates the presence of proteins. The intensity of the color, and hence the absorption at 546 nm, is directly proportional to the protein concentration, according to the Beer-Lambert law. The standardisation was performed using BSA (Bovine Serum Albumine) and the protein content was expressed in g protein as BSA equivalent/L or mg protein as BSA equivalent/ml. The protein content was calculated using standard calculation protocols known in the art, by plotting the $OD_{546}$ versus the concentration of samples with known concentration, followed by the calculation of the concentration of the unknown samples using the equation generated from the calibration line.

Methods for Determination of Beta-Glucosidase Activity

Beta-glucosidase activity was determined using para-nitrophenyl-beta-glucoside at 1.5 mM concentration in 50 mM sodium acetate buffer at pH 4.5. Incubation was performed at 40° C. for 30 min. Reaction was stopped using 1 M sodium bicarbonate. The activity was calculated from the extinction determined at 405 nm, and the molar extinction coefficient of para-nitrophenol at alkaline conditions, as is known by those skilled in the art. Activity is expressed as μmol pNP released per ml per minute. An alternative method for beta-glucosidase activity determination is the incubation of the enzyme with 10 mM cellobiose in 50 mM sodium acetate buffer. After 30 minutes at 40° C. the reaction is stopped with sodium hydroxide. Samples were ultrafiltrated and analysed using High Performance Anion Exchange Chromatography with Pulsed Amperometric Detetction (HPAEC-PAD). A Carbo-Pac PA-20 column thermostated at 30° C., and 200 mM NaOH at a flow rate of 0.5 ml/min were applied to separate glucose and cellobiose. The beta-glucosidase activity was expressed in pmol glucose released per ml per minute.

Preparation of Washed Pre-Treated Wheat Straw Substrate

Dilute-acid pre-treated wheat straw can be obtained as described in Linde, M. et al, Biomass and Bioenergy 32 (2008), 326-332 and equipment as described in Schell, D. J., Applied Biochemistry and Biotechnology (2003), vol. 105-108, pp 69-85, may be used. The pre-treated wheat straw was washed with water until the solution with wheat straw was pH 6.0 or higher. The wash water was filtered off.

Extended Hydrolysis of Cellulose

Incubations of enzyme combinations on 2% washed acid pretreated wheat straw (PWS) dry matter (dm) substrate solution in 50 mM sodium acetate buffer pH 4.5, were performed at 10 mL scale. Enzyme combinations were added at fixed protein dose per gram substrate dry matter. Samples were taken in time, until 72 hours of incubation at 65° C. The reactions were terminated at the given time, by spinning down the residue, pipetting of the supernatant and freezing the samples until analysis.

Analysis of the amount of glucose released was performed using flow-NMR. The $^1$H NMR spectra were recorded on a Bruker AVANCE II BEST NMR system operating at proton frequency 500 MHz and probe temperature 27° C.

Example 1

1.1. Construction of Expression Plasmids

The sequence having SEQ ID NO: 1 was cloned into the pGBTOP vector (FIG. 1) using EcoRI and SnaBI sites, comprising the glucoamylase promoter and terminator sequence. The *E. coli* part was removed by NotI digestion prior to transformation of *A. niger* CBS 513.88.

1.2. Transformation of *A. niger*

*A. niger* WT-1: This *A. niger* strain is CBS513.88 comprising deletions of the genes encoding glucoamylase (glaA), fungal amylase and acid amylase. *A. niger* WT 1 is constructed by using the "MARKER-GENE FREE" approach as described in EP 0 635 574 B1.

The expression constructs are co-transformed to strain *A. niger* WT-1 according to the method described by Tilburn, J. et al. (1983) Gene 26, 205-221 and Kelly, J. & Hynes, M. (1985) EMBO J., 4, 475-479 with the following modifications:

Spores are germinated and cultivated for 16 hours at 30 degrees Celsius in a shake flask placed in a rotary shaker at 300 rpm in *Aspergillus* minimal medium (100 ml). *Aspergillus* minimal medium contains per liter: 6 g $NaNO_3$, 0.52 g KCl, 1.52 g $KH_2PO_4$, 1.12 ml 4 M KOH, 0.52 g $MgSO_4.7H_2O$, 10 g glucose, 1 g casaminoacids, 22 mg $ZnSO_4.7H_2O$, 11 mg $H_3BO_3$, 5 mg $FeSO_4.7H_2O$, 1.7 mg $CoCl_2.6H_2O$, 1.6 mg $CuSO_4.5H_2O$, 5 mg $MnCl_2.2H_2O$, 1.5 mg $Na_2MoO_4.2H_2O$, 50 mg EDTA, 2 mg riboflavin, 2 mg thiamine-HCl, 2 mg nicotinamide, 1 mg pyridoxine-HCL, 0.2 mg panthotenic acid, 4 g biotin, 10 ml Penicillin (5000 IU/ml) Streptomycin (5000 UG/ml) solution (Gibco).

Novozym 234™ (Novo Industries) instead of helicase is used for the preparation of protoplasts;

After protoplast formation (60-90 minutes), KC buffer (0.8 M KCl, 9.5 mM citric acid, pH 6.2) is added to a final volume of 45 ml, the protoplast suspension is centrifuged for 10 minutes at 3000 rpm at 4 degrees Celsius in a swinging-bucket rotor. The protoplasts are resuspended in 20 ml KC buffer and subsequently 25 ml of STC buffer (1.2 M sorbitol, 10 mM Tris-HCl pH 7.5, 50 mM $CaCl_2$) iss added. The protoplast suspension is centrifuged for 10 minutes at 3000 rpm at 4 degrees Celsius in a swinging-bucket rotor, washed in STC-buffer and resuspended in STC-buffer at a concentration of 10E8 protoplasts/ml;

To 200 microliter of the protoplast suspension, the DNA fragment, dissolved in 10 microliter TE buffer (10 mM Tris-HCl pH 7.5, 0.1 mM EDTA) and 100 microliter of PEG solution (20% PEG 4000 (Merck), 0.8 M sorbitol, 10 mM Tris-HCl pH 7.5, 50 mM $CaCl_2$) is added;

After incubation of the DNA-protoplast suspension for 10 minutes at room temperature, 1.5 ml PEG solution (60% PEG 4000 (Merck), 10 mM Tris-HCl pH 7.5, 50 mM $CaCl_2$) is added slowly, with repeated mixing of the tubes. After incubation for 20 minutes at room temperature, suspensions are diluted with 5 ml 1.2 M sorbitol, mixed by inversion and centrifuged for 10 minutes at 4000 rpm at room temperature. The protoplasts are resuspended gently in 1 ml 1.2 M sorbitol and plated onto solid selective regeneration medium consisting of either *Aspergillus* minimal medium without riboflavin, thiamine.HCL, nicotinamide, pyridoxine, panthotenic acid, biotin, casaminoacids and glucose. In case of acetamide selection the medium contains 10 mM acetamide as the sole nitrogen source and 1 M sucrose as osmoticum and C-source. Alternatively, protoplasts are plated onto PDA (Potato Dextrose Agar, Oxoid) supplemented with 1-50 microgram/ml phleomycin and 1M sucrose as osmosticum. Regeneration plates are solidified using 2% agar (agar No. 1, Oxoid L11). After incubation for 6-10 days at 30 degrees Celsius, conidiospores of transformants are transferred to plates consisting of *Aspergillus* selective medium (minimal medium containing acetamide as sole nitrogen source in the case of acetamide selection or PDA supplemented with 1-50 microgram/ml phleomycin in the case of phleomycin selection) with 2% glucose and 1.5% agarose (Invitrogen) and incubated for 5-10 days at 30 degrees Celsius. Single transformants are isolated and this selective purification step is repeated once upon which purified transformants are stored.

After transformation, transformants were selected on media comprising acetamide as sole nitrogen source and colony purified. Copy numbers were estimated by quantitative-PCR and low and high copy number transformants were selected. High copy transformants were cultured in shake flasks in 100 ml of CSM-MES medium as described in EP 635 574 at 34° C. at 170 rpm in an incubator shaker using a 500 ml baffled shake flask. After 3 and 4 days of fermentation, supernatant samples were harvested to determine expression by SDS-PAGE.

1.3 Protein Content

The ultrafiltrated and concentrated supernatants of the shakeflask fermentations of the transformants expressing beta-glucosidase (TEMER06387) were analysed for protein content. The protein content was determined to be 4 mg protein as BSA equivalent/ml.

Example 2

2.1 Preparation of Cellulase Samples

A cellulase enhancing protein, TEMER07589 (As described in co-pending patent application DSM Case 27666, filed on same day as this application), and two exoglucanases, being CBHI as described in patent application EP09158739.4 and CBHII (As described in co-pending patent application DSM Case 27829, filed on same day as this application), all from *Talaromyces emersonii*, were prepared as described in Example 1 for TEMER06387. Protein contents of these samples were determined and ranged from 20 to 60 mg protein as BSA equivalent/ml. Additionally, one of the closest homologs of the beta-glucosidase TEMER06387, being a beta-glucosidase of *Sclerotinia sclerotiorum* (XP_001591700; NCBI) was also prepared as described above. This beta-glucosidase will be denoted as BG-SS.

2.2 Extended Hydrolysis of 4 Enzyme Mixes

The TEMER06387 beta-glucosidase was mixed with the 3 other cellulolytic proteins, at relative amounts of 9% of TEMER06387, 37% of TEMER07589, 30% of CBHI and 24% of CBHII, of the total protein in the mix. A similar mix was also prepared with the BG-SS, in which TEMER06387 was replaced by BG-SS. These mixes were applied in extended hydrolysis at 10 mL scale with 2% DM pretreated wheat straw, at pH 4.5 and 65° C. The total protein dose in each of the incubations was 15 mg protein as BSA equivalent per gram pretreated wheat straw dry matter. Incubations lasted 72 hours and at several time intervals samples were taken. Samples were spinned off, and supernatant was frozen until analysis by NMR. The release of glucose and cellobiose in time is shown in Table 1.

TABLE 1

Release of glucose and cellobiose, expressed as mmol/L, during incubation of 2% DM washed pretreated wheat straw, at pH 4.5 and 65° C., by a 4 enzyme mix containing 1 BG (TEMER06387 or BG-SS), 1 CBHI, 1 CBHII and 1 cellulase enhancing protein, at relative amounts of 9%, 30%, 24% and 37% of total protein of the mix.

|  | Glc (mmol/L) | | | | Cellobiose (mmol/L) | | | |
| --- | --- | --- | --- | --- | --- | --- | --- | --- |
|  | 3 h | 21 h | 45 h | 72 h | 3 h | 21 h | 45 h | 72 h |
| TEMER06387 mix | 13.5 | 26.5 | 32.7 | 37.2 | 0.1 | 0.7 | 0.9 | 0.6 |

From this experiment, it is clear that TEMER06387 is well able to hydrolyse cellulose to glucose in a mix with 3 other cellulolytic proteins.

The invention claimed is:

1. A variant polypeptide having at least 95% sequence identity with the sequence set out in SEQ ID NO: 2 or the mature form thereof, wherein said variant polypeptide or mature form thereof has one or more substitutions or insertions relative to SEQ ID NO: 2 and wherein said variant polypeptide has beta-glucosidase activity.

2. A polynucleotide which encodes the polypeptide according to claim 1, or the reverse complement thereof.

3. The polynucleotide according to claim 2 which encodes a polypeptide.

4. The polynucleotide according to claim 2 which is a DNA sequence.

5. A nucleic acid construct comprising the polynucleotide according to claim 2.

6. The nucleic acid construct according to claim 5, wherein the GC content is at least 56%, at least 58%, or from 58-65%.

7. A vector incorporating a polynucleotide sequence encoding a polypeptide having at least 95% sequence identity with the sequence set out in SEQ ID NO: 2, or the mature form thereof; and a heterologous polynucleotide sequence, wherein said polypeptide has beta-glucosidase activity.

8. A cell comprising the vector according to claim 7.

9. The cell according to claim 8, wherein the cell is a eukaryotic cell.

10. The cell according to claim 9 wherein the cell is a fungal cell.

11. The cell according to claim 10 wherein the fungal cell is selected from the group consisting of the genera *Aspergillus*, *Trichoderma/Hypocrea*, *Fusarium*, *Disporotrichum*, *Penicillium*, *Acremonium*, *Neurospora*, *Thermoascus*, *Myceliophtora*, *Sporotrichum*, *Thielavia*, *Chrysosporium*, *Fusarium*, *Humicola*, *Neurospora* and *Talaromyces*.

12. The cell according to claim 11, wherein the fungal cell is of the species *Aspergillus oryzae*, *Aspergillus sojae*, *Aspergillus nidulans*, or *Aspergillus niger*.

13. The cell according to claim 8, wherein at least one gene is deleted, knocked-out or disrupted in full or in part, wherein the at least one gene that is deleted, knocked-out or disrupted in full or in part is selected from the group consisting of a protease, hdfA, hdfB, prtT, glucoamylase, neutral alpha-amylase A, neutral alpha-amylase B, oxalic acid hydrolase, and a toxin selected from the group consisting or ochratoxins, fumonisins, cyclapiazonic acid, 3-nitropropionic acid, emodin, malformin, alfatoxins and secalonic acids.

14. A transgenic plant or part thereof which comprises the polynucleotide according to claim 2, wherein optionally the plant is a corn plant, a sorghum plant, a tomato plant, a wheat plant, an oilseed plant, a rapeseed plant, a soybean plant, a barley plant, a grass, or a tobacco plant; or a plant of the genera *Anacardium*, *Arachis*, *Ragus*, *Atropa*, *Avena*, *Brassica*, *Citrus*, *Citrullus*, *Capsicum*, *Carthamus*, *Cocos*, *Coffea*, *Cucumis*, *Cucurbita*, *Oaucus*, *Elaeis*, *Fragaria*, *Glycine*,

*Gossypium, Helianthus, Ocallis, Hordeum, Hyoscyamus, Lactuca, Linum, Lolium, Lupinus, Lycopersicon, Malus, Majorana, Medicago, Nicotiana, Olea, Oryza, Panieum, Pannisetum, Persea, Eolus, Pistachio, Pisum, Pyrus, Prunus, Raphanus, Ricinus, Secale, Senecio, Sinapis, Sorghum, Theobromus, Trigonella, Triticum, Vicia, Vitis, Vigna* or *Zea.*

15. A method for preparing a polypeptide comprising the amino acid sequence set out in SEQ ID NO: 2 or the mature form thereof, or an amino acid sequence having at least 95% sequence identity with the sequence set out in SEQ ID NO: 2 or the mature form thereof, wherein said method comprises cultivating the cell of claim 8 under conditions which allow for expression of said polypeptide and, optionally, recovering the expressed polypeptide.

16. A composition comprising: (i) a polypeptide having at least 95% sequence identity with the sequence set out in SEQ ID NO: 2, or the mature form thereof, wherein said polypeptide has beta-glucosidase activity and; (ii) a cellulase and/or a hemicellulase and/or a pectinase and/or a polypeptide belonging to family GH61.

17. The composition according to claim 16, wherein the cellulase is a cellobiohydrolase, cellobiohydrolase I, cellobiohydrolase II, an endo-β-1,4-glucanase, a β-glucosidase or a β-(1,3)(1,4)-glucanase.

18. The composition according to claim 16, wherein the hemicellulase is an endoxylanase, a β-xylosidase, a a-L-arabinofuranosidase, an a-D-glucuronidase, an acetyl xylan esterase, a feruloyl esterase, a coumaroyl esterase, an a-galactosidase, a β-galactosidase, a β-mannanase or a β-mannosidase.

19. The composition according to claim 16, wherein the pectinase is an endo polygalacturonase, a pectin methyl esterase, an endo-galactanase, a beta galactosidase, a pectin acetyl esterase, an endo-pectin lyase, pectate lyase, alpha rhamnosidase, an exo-galacturonase, an expolygalacturonate lyase, a rhamnogalacturonan hydrolase, a rhamnogalacturonan lyase, a rhamnogalacturonan acetyl esterase, a rhamnogalacturonan galacturonohydrolase, a xylogalacturonase, an alpha-arabinofuranosidase or an endo-arabinanase.

20. The composition according to claim 16 further comprising a ligninase, an expansin, an expansin-like polypeptide, a swollenin or a polypeptide product of a gene encoding a cellulose integrating protein or a cellulose induced protein.

21. A method for treating a substrate comprising carbohydrate material, optionally a plant material, which method comprises a) contacting the substrate with a polypeptide having at least 95% sequence identity with the sequence set out in SEQ ID NO: 2, or the mature form thereof, wherein said polypeptide has beta-glucosidase activity; or b) a composition comprising a polypeptide having at least 95% sequence identity with the sequence set out in SEQ ID NO: 2, or the mature form thereof, wherein said polypeptide has beta-glucosidase activity; and a cellulase and/or a hemicellulase and/or a pectinase and/or a polypeptide belonging to family GH61.

22. The method according to claim 21, wherein the substrate is a plant material and the plant material is provided in the form of a plant, a plant pulp, a plant extract, a foodstuff and/or ingredient derived there from and/or a fabric, textile and/or item of clothing comprising a plant material.

23. The method according to claim 21, wherein the treating comprises degradation and/or modification of cellulose and/or hemicellulose and/or a pectic substance.

24. The polypeptide according to claim 1 that is capable of producing sugar from a ligno-cellulosic material.

25. A fusion protein comprising the mature form of SEQ ID NO: 2 fused to a heterologous secretion leader sequence.

26. The fusion protein according to claim 25, wherein the heterologous secretion leader sequence is selected from a fungal amyloglucosidase (AG) gene; an α-factor gene, or an α-amylase gene.

27. A process for the preparation of a fermentation product, which process comprises:

a) degrading lignocellulose by contacting the lignocellulose with a polypeptide having at least 95% sequence identity with the sequence set out in SEQ ID NO: 2, or the mature form thereof wherein said polypeptide has beta-glucosidase activity; or a composition comprising a polypeptide having at least 95% sequence identity with the sequence set out in SEQ ID NO: 2, or the mature form thereof wherein said polypeptide has beta-glucosidase activity, and a cellulase and/or a hemicellulase and/or a pectinase, b) fermenting the resulting material to prepare a fermentation product, and c) optionally, recovering the fermentation product.

28. The process of claim 27, wherein the fermentation product recovered in step (c) is ethanol.

* * * * *

SEQUENCE LISTING

<160> NUMBER OF SEQ ID NOS: 6

<210> SEQ ID NO 1
<211> LENGTH: 2541
<212> TYPE: DNA
<213> ORGANISM: Talaromyces emersonii

<400> SEQUENCE: 1

```
atgcagttcc tcgtgcctct cctgctgttt ctctcactct gcttaggcca acaaaatgaa      60
ggatctgtat acaccccccg gataagctca ggctatggca attggtctga agcatacaga     120
aaagcccgcg aattcgtctg tcagttaacg ttgaccgaaa aagtcaacct cacaacgcaa     180
gtcggcacgg gccagaccca aggctacgac attggcatca tcccccggct gaactttcga     240
ggatttgcgg ctgatgactc gccctccggc gtgcgaggaa ccgactattc ctccgccttt     300
gcggcgggac ttaacctggc catgtcctgg gatagagagc taatctatgc tcaatcatac     360
gccaacggag cggagcacaa gggcaaaggc gtcaatatcg tctatgcccc cgtggccggt     420
ccgctggggc gagcgccaac cgggggggcgc attttcgaga gctactctcc agatccgtat     480
ctctcaggga tcgccttcgg gacatcgatt gcaggaatgc aggctgccgg agtgatcgcc     540
gtcgggaaac acttcatcct ctatgagcag gagcatttcc gccaagtcat cgaatggaac     600
tcgtacgggc tgggcccgaa tatcacggag ccgtactcgt cgaactgtga tgaccggact     660
ttgcacgagc tctatctgtt cccgtggtac gacgctgtat acagcggcat ggccggggtg     720
atgtgttcct acaaccagat caacaatacc caggcgtgcc agaacaatca catcctgaat     780
gacatcctca agggcgaact cggcttccag gggtttgtga ccagcgacga cgggtcccag     840
cacgacggag tcctcaccgc gctggcagga atggacatga ctattcctgg agagacctct     900
ccgaacggta tcgccgggct agggatctca ttctgggggc caatctcac catggccgtg     960
ctcaatggca gcgtgcccga gtggcggctt gacgacatgg ccaccaggat tatggctgct    1020
tactactacc tcgccagga ccaggatttc ccaccactga gctttgcagc agcagattac    1080
tctacgtacg gatacgagta tccgcaagcg caggtcgact acacgcagat caactggcac    1140
gtcgatgtgc gtcagaatca ctctcagatc atccgtgcgg tgggcgccaa ctcgatcgtg    1200
ctgctgaaga ataacaacgg cacgcttcct ctcaggaaac ccagacagat tgccgtcatc    1260
ggcgaggatg ctggtccttc gccctacggt cccaacggct gcactgatcg gggctgcgtt    1320
aatggcacgc ttgcgatggg ctgggggagt ggtagcacaa atttcccgta tctggtcgac    1380
cccttgtctg ccatccagca gcgggcgttg aaagacggta ccgaagtgca atatgtcttg    1440
aataatttcg ccactgcgca gatcgactct gtagcgtcgc aagccaccgt gtgtctcgtg    1500
ttcatcaatg ccgatagcgg agagggatat atcgaggtgg gcggcaacta cggcgacagg    1560
aacaatctca cggcatggct gggcggagat gctctcgtcc aacgggttgc tgcgaactgc    1620
agtcagacgg cggtcatcat ccatgcgcca gggcccattc tgatgaggga ctggatcgac    1680
cacccgaatg tgacggcggt gctctttgcc gggctcccgg acaggaaag cgggaatttg    1740
ctggtcgacg tgctgtacgg cgacgtcaac ccatctggca aacttccctg gaccgtgggc    1800
aaggctcgcg aggactacgg gactgatgtg ttgtatgaac ccaaagggcc agtgccgcag    1860
atcgacttca cagagggcct gttcatcgac tatcgctggt tcgacaagca gggcatcgat    1920
cctcgctttg aattcggctt tgggctgagc tacacgacgt tcgactatca gaacctcagc    1980
atcgagacct taaaagcctc tccagcgaca gcaacaacca tcgccagt agcttcaacc    2040
accgtcaatc cttctaggtg cccgaccacc agcctcaatc cgtccgacta cacgtttcca    2100
tcgacgatca gctcgctgac gaattacatc tacccgtaca tcgctcccaa tgcgacaatc    2160
tctaccgctg ccgccggtac accgacgccc actatcatcc cggaggcagc aggtcctcag    2220
ggaggaaacc cggcgttgta cgatgtgctg taccgggtga cattgacgct gaagaacaac    2280
ggaaccgttg cggggcaaga ggtggcccag ctgtatctgg acttggacaa tggggagccc    2340
```

```
agtcgccagc ttcgggggtt caacaagacg ttcctgcagg ccggggagac caaggacgtc    2400
acgtttgatc tgcggaggag agatgtggcg atttgggatg ttgtgaagca ggagtgggtc    2460
gaggtcaaga aactggggac aaagattggg gtgtatgttg gggccagctc gagggatttg    2520
cgtctgacgg gggagatctg a                                              2541
```

<210> SEQ ID NO 2
<211> LENGTH: 846
<212> TYPE: PRT
<213> ORGANISM: Talaromyces emersonii

<400> SEQUENCE: 2

```
Met Gln Phe Leu Val Pro Leu Leu Phe Leu Ser Leu Cys Leu Gly
1               5                   10                  15

Gln Gln Asn Glu Gly Ser Val Tyr Thr Pro Arg Ile Ser Ser Gly Tyr
            20                  25                  30

Gly Asn Trp Ser Glu Ala Tyr Arg Lys Ala Arg Glu Phe Val Cys Gln
        35                  40                  45

Leu Thr Leu Thr Glu Lys Val Asn Leu Thr Thr Gln Val Gly Thr Gly
    50                  55                  60

Gln Thr Gln Gly Tyr Asp Ile Gly Ile Ile Pro Arg Leu Asn Phe Arg
65                  70                  75                  80

Gly Phe Ala Ala Asp Asp Ser Pro Ser Gly Val Arg Gly Thr Asp Tyr
                85                  90                  95

Ser Ser Ala Phe Ala Ala Gly Leu Asn Leu Ala Met Ser Trp Asp Arg
            100                 105                 110

Glu Leu Ile Tyr Ala Gln Ser Tyr Ala Asn Gly Ala Glu His Lys Gly
        115                 120                 125

Lys Gly Val Asn Ile Val Tyr Ala Pro Val Ala Gly Pro Leu Gly Arg
    130                 135                 140

Ala Pro Thr Gly Gly Arg Ile Phe Glu Ser Tyr Ser Pro Asp Pro Tyr
145                 150                 155                 160

Leu Ser Gly Ile Ala Phe Gly Thr Ser Ile Ala Gly Met Gln Ala Ala
                165                 170                 175

Gly Val Ile Ala Val Gly Lys His Phe Ile Leu Tyr Glu Gln Glu His
            180                 185                 190

Phe Arg Gln Val Ile Glu Trp Asn Ser Tyr Gly Leu Gly Pro Asn Ile
        195                 200                 205

Thr Glu Pro Tyr Ser Ser Asn Cys Asp Asp Arg Thr Leu His Glu Leu
    210                 215                 220

Tyr Leu Phe Pro Trp Tyr Asp Ala Val Tyr Ser Gly Met Ala Gly Val
225                 230                 235                 240

Met Cys Ser Tyr Asn Gln Ile Asn Asn Thr Gln Ala Cys Gln Asn Asn
                245                 250                 255

His Ile Leu Asn Asp Ile Leu Lys Gly Glu Leu Gly Phe Gln Gly Phe
            260                 265                 270

Val Thr Ser Asp Asp Gly Ser Gln His Asp Gly Val Leu Thr Ala Leu
        275                 280                 285

Ala Gly Met Asp Met Thr Ile Pro Gly Glu Thr Ser Pro Asn Gly Ile
    290                 295                 300

Ala Gly Leu Gly Ile Ser Phe Trp Gly Pro Asn Leu Thr Met Ala Val
305                 310                 315                 320

Leu Asn Gly Ser Val Pro Glu Trp Arg Leu Asp Asp Met Ala Thr Arg
                325                 330                 335
```

```
Ile Met Ala Ala Tyr Tyr Leu Gly Gln Asp Gln Asp Phe Pro Pro
            340                 345                 350

Leu Ser Phe Ala Ala Asp Tyr Ser Thr Tyr Gly Tyr Glu Tyr Pro
        355                 360                 365

Gln Ala Gln Val Asp Tyr Thr Gln Ile Asn Trp His Val Asp Val Arg
370                 375                 380

Gln Asn His Ser Gln Ile Ile Arg Ala Val Gly Ala Asn Ser Ile Val
385                 390                 395                 400

Leu Leu Lys Asn Asn Asn Gly Thr Leu Pro Leu Arg Lys Pro Arg Gln
                405                 410                 415

Ile Ala Val Ile Gly Glu Asp Ala Gly Pro Ser Pro Tyr Gly Pro Asn
            420                 425                 430

Gly Cys Thr Asp Arg Gly Cys Val Asn Gly Thr Leu Ala Met Gly Trp
        435                 440                 445

Gly Ser Gly Ser Thr Asn Phe Pro Tyr Leu Val Asp Pro Leu Ser Ala
    450                 455                 460

Ile Gln Gln Arg Ala Leu Lys Asp Gly Thr Glu Val Gln Tyr Val Leu
465                 470                 475                 480

Asn Asn Phe Ala Thr Ala Gln Ile Asp Ser Val Ala Ser Gln Ala Thr
                485                 490                 495

Val Cys Leu Val Phe Ile Asn Ala Asp Ser Gly Glu Gly Tyr Ile Glu
            500                 505                 510

Val Gly Gly Asn Tyr Gly Asp Arg Asn Asn Leu Thr Ala Trp Leu Gly
        515                 520                 525

Gly Asp Ala Leu Val Gln Arg Val Ala Ala Asn Cys Ser Gln Thr Ala
    530                 535                 540

Val Ile Ile His Ala Pro Gly Pro Ile Leu Met Glu Asp Trp Ile Asp
545                 550                 555                 560

His Pro Asn Val Thr Ala Val Leu Phe Ala Gly Leu Pro Gly Gln Glu
                565                 570                 575

Ser Gly Asn Leu Leu Val Asp Val Leu Tyr Gly Asp Val Asn Pro Ser
            580                 585                 590

Gly Lys Leu Pro Trp Thr Val Gly Lys Ala Arg Glu Asp Tyr Gly Thr
        595                 600                 605

Asp Val Leu Tyr Glu Pro Lys Gly Pro Val Pro Gln Ile Asp Phe Thr
    610                 615                 620

Glu Gly Leu Phe Ile Asp Tyr Arg Trp Phe Asp Lys Gln Gly Ile Asp
625                 630                 635                 640

Pro Arg Phe Glu Phe Gly Phe Gly Leu Ser Tyr Thr Thr Phe Asp Tyr
                645                 650                 655

Gln Asn Leu Ser Ile Glu Thr Leu Lys Ala Ser Pro Ala Thr Ala Thr
            660                 665                 670

Thr Thr Ser Pro Val Ala Ser Thr Thr Val Asn Pro Ser Arg Cys Pro
        675                 680                 685

Thr Thr Ser Leu Asn Pro Ser Asp Tyr Thr Phe Pro Ser Thr Ile Ser
    690                 695                 700

Ser Leu Thr Asn Tyr Ile Tyr Pro Tyr Ile Ala Pro Asn Ala Thr Ile
705                 710                 715                 720

Ser Thr Ala Ala Ala Gly Thr Pro Thr Pro Thr Ile Ile Pro Glu Ala
                725                 730                 735

Ala Gly Pro Gln Gly Gly Asn Pro Ala Leu Tyr Asp Val Leu Tyr Arg
            740                 745                 750
```

```
Val Thr Leu Thr Leu Lys Asn Asn Gly Thr Val Ala Gly Gln Glu Val
        755                 760                 765

Ala Gln Leu Tyr Leu Asp Leu Asp Asn Gly Glu Pro Ser Arg Gln Leu
    770                 775                 780

Arg Gly Phe Asn Lys Thr Phe Leu Gln Ala Gly Glu Thr Lys Asp Val
785                 790                 795                 800

Thr Phe Asp Leu Arg Arg Arg Asp Val Ala Ile Trp Asp Val Val Lys
                805                 810                 815

Gln Glu Trp Val Glu Val Lys Lys Leu Gly Thr Lys Ile Gly Val Tyr
            820                 825                 830

Val Gly Ala Ser Ser Arg Asp Leu Arg Leu Thr Gly Glu Ile
        835                 840                 845

<210> SEQ ID NO 3
<211> LENGTH: 16
<212> TYPE: PRT
<213> ORGANISM: Talaromyces emersonii

<400> SEQUENCE: 3

Met Gln Phe Leu Val Pro Leu Leu Leu Phe Leu Ser Leu Cys Leu Gly
1               5                   10                  15

<210> SEQ ID NO 4
<211> LENGTH: 10
<212> TYPE: DNA
<213> ORGANISM: Artificial Sequence
<220> FEATURE:
<223> OTHER INFORMATION: Translational initiator sequence
<220> FEATURE:
<221> NAME/KEY: misc_feature
<222> LOCATION: (1)..(1)
<223> OTHER INFORMATION: n = "m" where "m" is A or C
<220> FEATURE:
<221> NAME/KEY: misc_feature
<222> LOCATION: (2)..(2)
<223> OTHER INFORMATION: n = "w" where "w" is A or T
<220> FEATURE:
<221> NAME/KEY: misc_feature
<222> LOCATION: (4)..(4)
<223> OTHER INFORMATION: n = "h" where "h" is A or C or T
<220> FEATURE:
<221> NAME/KEY: misc_feature
<222> LOCATION: (5)..(5)
<223> OTHER INFORMATION: n = "k" where "k" is G or T
<220> FEATURE:
<221> NAME/KEY: misc_feature
<222> LOCATION: (6)..(6)
<223> OTHER INFORMATION: n = "y" where "y" is C or T

<400> SEQUENCE: 4 nncnnncaaa                                                                10

<210> SEQ ID NO 5
<211> LENGTH: 10
<212> TYPE: DNA
<213> ORGANISM: Artificial Sequence
<220> FEATURE:
<223> OTHER INFORMATION: Translational initiator sequence
<220> FEATURE:
<221> NAME/KEY: misc_feature
<222> LOCATION: (1)..(1)
<223> OTHER INFORMATION: n = "m" where "m" is A or C
<220> FEATURE:
<221> NAME/KEY: misc_feature
<222> LOCATION: (2)..(2)
<223> OTHER INFORMATION: n = "w" where "w" is A or T
<220> FEATURE:
<221> NAME/KEY: misc_feature
<222> LOCATION: (4)..(4)
```

```
<223> OTHER INFORMATION: n = "h" where "h" is A or C or T
<220> FEATURE:
<221> NAME/KEY: misc_feature
<222> LOCATION: (5)..(5)
<223> OTHER INFORMATION: n = "k" where "k" is G or T
<220> FEATURE:
<221> NAME/KEY: misc_feature
<222> LOCATION: (6)..(6)
<223> OTHER INFORMATION: n = "y" where "y" is C or T

<400> SEQUENCE: 5 nncnnncaca                                                                    10

<210> SEQ ID NO 6
<211> LENGTH: 10
<212> TYPE: DNA
<213> ORGANISM: Artificial Sequence
<220> FEATURE:
<223> OTHER INFORMATION: Translational initiator sequence
<220> FEATURE:
<221> NAME/KEY: misc_feature
<222> LOCATION: (1)..(1)
<223> OTHER INFORMATION: n = "m" where "m" is A or C
<220> FEATURE:
<221> NAME/KEY: misc_feature
<222> LOCATION: (2)..(2)
<223> OTHER INFORMATION: n = "w" where "w" is A or T
<220> FEATURE:
<221> NAME/KEY: misc_feature
<222> LOCATION: (4)..(4)
<223> OTHER INFORMATION: n = "h" where "h" is A or C or T
<220> FEATURE:
<221> NAME/KEY: misc_feature
<222> LOCATION: (5)..(5)
<223> OTHER INFORMATION: n = "k" where "k" is G or T
<220> FEATURE:
<221> NAME/KEY: misc_feature
<222> LOCATION: (6)..(6)
<223> OTHER INFORMATION: n = "y" where "y" is C or T

<400> SEQUENCE: 6 nncnnncaag                                                                    10
```